(12) United States Patent
Jolidon et al.

(10) Patent No.: US 7,173,023 B2
(45) Date of Patent: Feb. 6, 2007

(54) BICYCLIC COMPOUNDS

(75) Inventors: Synese Jolidon, Blauen (CH); Rosa Maria Rodriguez Sarmiento, Basel (CH); Andrew William Thomas, Birsfelden (CH); Wolfgang Wostl, Grenzach-Wyhlen (DE); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 33 days.

(21) Appl. No.: 10/967,567

(22) Filed: Oct. 18, 2004

(65) Prior Publication Data

US 2005/0107360 A1  May 19, 2005

(30) Foreign Application Priority Data

Oct. 23, 2003  (EP)  ............................ 03024297

(51) Int. Cl.
A61K 31/55 (2006.01)
C07D 223/16 (2006.01)
C07D 487/02 (2006.01)

(52) U.S. Cl. .................. 514/217.01; 514/212.07; 540/523; 540/594

(58) Field of Classification Search ............ 540/594; 514/217.01
See application file for complete search history.

(56) References Cited

U.S. PATENT DOCUMENTS

| | | | |
|---|---|---|---|
| 3,719,669 A * | 3/1973 | Shetty | 540/594 |
| 4,210,749 A * | 7/1980 | Shetty | 540/594 |
| 4,287,351 A | 9/1981 | Bourgery et al. | |
| 4,524,206 A | 6/1985 | New et al. | |
| 4,764,522 A | 8/1988 | Kyburz et al. | |
| 4,776,876 A | 10/1988 | Nordhoff et al. | |
| 4,906,626 A | 3/1990 | Amrein et al. | |
| 5,100,914 A | 3/1992 | Rendenbach-Mueller et al. | |
| 5,304,556 A | 4/1994 | Yamamoto et al. | |
| 5,317,017 A * | 5/1994 | Ok et al. | 514/211.06 |
| 5,416,112 A | 5/1995 | Kuo | |
| 5,446,066 A | 8/1995 | Varasi et al. | |
| 5,731,324 A | 3/1998 | Fisher | |
| 5,889,026 A | 3/1999 | Alanine et al. | |
| 6,020,362 A | 2/2000 | Fisher | |
| 6,137,002 A | 10/2000 | Fisher et al. | |
| 6,448,269 B1 | 9/2002 | Fisher et al. | |
| 6,472,405 B1 | 10/2002 | Fisher | |
| 6,660,736 B2 | 12/2003 | Cesura et al. | |
| 6,667,327 B2 | 12/2003 | Cesura et al. | |
| 6,762,320 B2 | 7/2004 | Jolidon et al. | |
| 6,818,774 B2 | 11/2004 | Cesura et al. | |
| 6,953,787 B2 * | 10/2005 | Smith et al. | 514/212.02 |

FOREIGN PATENT DOCUMENTS

| | | |
|---|---|---|
| DE | 1003753 | 3/1957 |
| EP | 0326023 | 8/1989 |
| EP | 03633793 | 4/1990 |
| EP | 0400495 | 12/1990 |
| EP | 0504574 | 9/1992 |
| EP | 0632017 | 1/1995 |
| EP | 0635492 | 1/1995 |
| EP | 0754455 | 1/1997 |
| EP | 0985665 | 3/2000 |
| FR | 2500831 | 9/1982 |
| FR | 2645019 | 10/1990 |
| JP | 2-142774 | 5/1990 |
| JP | 5-262718 | 10/1993 |
| WO | WO 90/11997 | 10/1990 |
| WO | WO 99/14334 | 11/1990 |
| WO | WO 92/05163 | 4/1992 |
| WO | WO 9304686 A1 * | 3/1993 |
| WO | WO 96/22288 | 7/1996 |
| WO | WO 96/40095 | 12/1996 |
| WO | WO 97/05102 | 2/1997 |
| WO | WO 97/33572 | 9/1997 |
| WO | WO 99/10349 | 3/1999 |
| WO | WO 99/26614 | 6/1999 |
| WO | WO 99/35123 | 7/1999 |

(Continued)

OTHER PUBLICATIONS

Citation "O", WO2005/082859A1 is not being furnished with this Action because the publication is 550+ pages. See HCAPLUS, Accession No. 2005 979618 Attached to Action.*

(Continued)

Primary Examiner—Joseph K. McKane
Assistant Examiner—Nyeemah Grazier
(74) Attorney, Agent, or Firm—George W. Johnston; Patricia S. Rocha-Tramaloni; Kimberly J. Prior

(57) ABSTRACT

The present invention relates to novel benzazepine derivatives of the following formula:

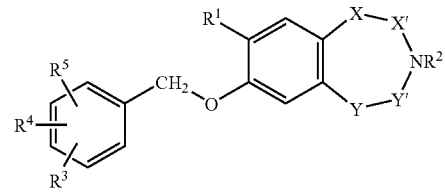

wherein $R^1$, $R^2$, $R^3$, $R^4$ and $R^5$, X, X', Y and Y' are as defined in the description and claims, processes for their preparation, pharmaceutical compositions containing said derivatives and their use for the preparation of medicaments useful for the prevention and treatment of diseases in which selective inhibition of monoamine oxidase B activity plays a role or is implicated.

37 Claims, No Drawings

FOREIGN PATENT DOCUMENTS

| | | |
|---|---|---|
| WO | WO 99/54279 | 10/1999 |
| WO | WO 00/75106 | 12/2000 |
| WO | WO 01/32649 | 5/2001 |
| WO | WO 01/34172 | 5/2001 |
| WO | WO 01/56560 | 8/2001 |
| WO | WO 03/080573 | 10/2003 |
| WO | WO 03/080573 A1 | 10/2003 |
| WO | WO 2004/056369 A1 | 7/2004 |
| WO | WO 2005042491 A1 * | 5/2005 |

OTHER PUBLICATIONS

Bach, A. W. J., et al. Proc. Natl. Acad. Sci. USA 85:4934-4938 (1988).
Cesura, A. M., & Pletscher, A., Prog. Drug Research 38:171-297 (1992).
Fowler, C. J., et al. J. Neural. Transm. 49:1-20 (1980).
Benedetti, M. S., et al. Biochem. Pharmacol. 38:555-561 (1989).
Saura, J., et al. Neuroscience 70:755-774 (1996).
Bentué-Ferrer, D., et al. CNS Drugs 6(3): 217-236 (1996).
Gardner, D. M., et al. J. Clin. Psychiatry 57(3):99-104 (1996).
Cesura, et al., Eur J. Pharmacol. vol. 162, pp. 457-465 (1989).
Pecherer B. et al., J. Heterocycl. Chem. vol. 8(5) pp. 779-783 (1971).
Reiffen et al., J. Med. Chem. vol. 33(5) pp. 1496-1504 (1990).
Mannekens, E. et al., Synthesis vol. 9, pp. 1214-1216 (2000).
Fukumi, H. et al., Heterocycles vol. 9(9) pp. 1197-1206 (1978).
Fürstner, A. et al., Chemistry, A European Journal vol. 7(24) pp. 5286-5298 (2001).
Roy, S.C., et al, Tetrahedron Letters vol. 42(52) p. 9253-9255 (2001).
Suzuki, H. et al., Synthesis vol. 3, pp. 236-238 (1988).
Judeh, Z. M. et al., Tetrahedron Letters, vol. 43(29) pp. 5089-5091 (2002).
Okuda, K. et al., Bioorg. Med. Chem. Letters vol. 13(17) pp. 2853-2855 (2003).
J. Org. Chem. vol. 53, No. 24, pp. 5793-5796 (1988).
Zhou, M., & Panchuk-Voloshina, N., Analytical Biochemistry 253:169-174 (1997).
Schlaeger, E. J., & Christensen, K., Cytotechnology 30:71-83 (1999).
Grethe et al., J. Org. Chem. 33: 494-503 (1968).
Gnerre C. et al., Journal of Med. Chem. vol. 43 No. 25 pp. 4747-4758 (2000).
Cahn et al., Angew Chem. vol. 5, No. 4 pp. 385-415 (1966).
Cahn & Ingold, J. Chem. Soc. (London) pp. 612-622 (1951).
Cahn, et al., Experientia, vol. 12, pp. 81-124 (1956).
Cahn, J. Chem. Educ. vol. 41, pp. 116-125 (1964).
Fisher et al., Bioorganic and Medicinal Chem. Ltrs. vol. 7, No. 19 pp. 2537-2542 (1997).
Kalgutkar et al., Medicinal Research Reviews vol. 15, No. 4 pp. 325-388 (1995).
Foley, et al., Elsevier Science vol. 6, No. 1 pp. 25-47 (2000) (XP00087269).
Bentley et al., J. Chem. Soc. (C) 1969, pp. 2233-2234.
Krishnamurthy et al., Tetrahedron Lett. 1982, 23, pp. 3315-3318.
Lam et al., Tetrahedron Lett., 2002, 43, pp. 3091-3094.
Lam et al., Synlett, 2000, 5, pp. 674-676.
Chan et al., Tetrahedron Lett. 1998, 39, pp. 2933-2936.
Wolfe, J. P. ,et al. J. Amer. Chem. Soc. 118:7215-7216 (1996).
Ehrhardt, J. D. et al., European Journal of Medicinal Chem. vol. 13(3) pp. 235-240 (1978) (XP009018741).
Trivedi, J. P. et al., Indian Journal of Applied Chemistry, vol. 30(3-4) pp. 91-95 (1967) (XP009018747).
Lukas, A. et al., Acta Facultatis Pharm. Univ. Comenianae vol. 28, pp. 91-114 (1975) (XP00155612).
Lukas A. et al., Ceskoslov. Farm. vol. 13 pp. 225-228 (1964) (XP009018756).
Lukas, A. et al., Ceskoslov. Farm. vol. 21, No. 6, pp. 273-275. (1972) (XP009018758).
Lukas A. et al., Acta Facultatis Pharm. Bohemoslovenicae, vol. 12 pp. 189-202 (1966) (XP001155535).
Dostert P. et al., International Congress Series vol. 564, pp. 197-208 (1982) (XP001027632).
Abstract corresponding to JP 5-262718 (B24).
Greenspan et al. J. Med. Chem. 42: p. 164-172 (1999).
Drechsler et al., Eur. J. Org. Chem. p. 3441-3453 (1999).
Austin et al., J. Org. Chem. 46: p. 2280-2286 (1981).
Eckert et al., Synth. Commun. 28(2), pp. 327-335 (1998).
Jaen, J. et al., J. Med. Chem. 31: p. 1621-1625 (1988).
Rano, T. et al., Tetrahedron Letters vol. 36(22) pp. 3789-3792 (1995).
Ikuta, H., et al. J. Med. Chem. 30:1995-1998 (1987).
Danishefsky, S., et al. J. Amer. Chem. Soc. 97:3239-3241 (1975).
Freidinger, R. M., et al. J. Org. Chem. 47:104-109 (1982).
Abstract Corresponding to EP 0 985 665.
Ishibashi et al., Chem. Pharm Bull. vol. 37(4) pp. 939-943 (1989).
Abstract corresponding to JP 2-142774 (B7).
Abstract corresponding to WO 90/11997 (B27).
Abstract corresponding to FR 2500831 (B29).
Abstract corresponding to WO 01/32649 (B5).
Abstract corresponding to WO 90/11997 (B26).
Abstract corresponding to DE 1 003 753 (B22).

* cited by examiner

BICYCLIC COMPOUNDS

FIELD OF THE INVENTION

The present invention relates to the treatment of diseases mediated by or associated with monoamine oxidase B.

BACKGROUND OF THE INVENTION

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzyme exists in two forms, MAO-A and MAO-B, encoded by different genes (A. W. Bach et al., *Proc. Natl. Acad. Sci. USA* 1988, 85, 4934–4938) and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain (A. M. Cesura and A. Pletscher, Prog. Drug Research 1992, 38, 171–297). Brain MAO-B activity appears to increase with age. This increase has been attributed to the gliosis associated with aging (C. J. Fowler et al., *J. Neural. Transm.* 1980, 49, 1–20). Additionally, MAO-B activity is significantly higher in the brains of patients with Alzheimer's disease (P. Dostert et al., *Biochem. Pharmacol.* 1989, 38, 555–561) and it has been found to be highly expressed in astrocytes around senile plaques (Saura et al., *Neuroscience* 1994, 70, 755–774). In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by D. Bentue-Ferrer et al. in *CNS Drugs* 1996, 6, 217–236. Whereas a major limitation of irreversible and non-selective MAO inhibitor activity is the need to observe dietary precautions due to the risk of inducing a hypertensive crisis when dietary tyramine is ingested, as well as the potential for interactions with other medications (D. M. Gardner et al., *J. Clin. Psychiatry* 1996, 57, 99–104), these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

The present invention relates to novel benzazepine derivatives, processes for their preparation, pharmaceutical compositions containing said derivatives and their use in the prevention and treatment of diseases.

In particular, the present invention provides a compound of formula I

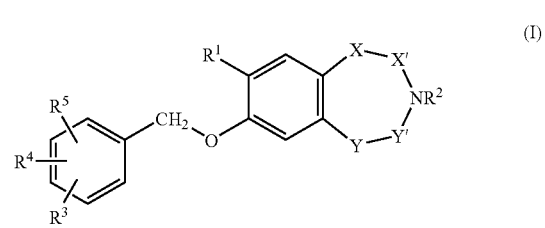

wherein
$R^1$ is hydrogen or methyl;
$R^2$ is hydrogen, $(C_1-C_3)$-alkyl, $-CH_2C(O)NH_2$, $-CH(CH_3)C(O)NH_2$, $-S(O)_2CH_3$ or $-C(O)R^6$;
$R^3$, $R^4$ and $R^5$ are each independently hydrogen, halogen, cyano, $(C_1-C_3)$-alkyl or $-O-(C_1-C_3)$-alkyl;
$R^6$ is hydrogen, $-CH_3$, $-CH_2OCH_3$, $-C(O)NH_2$, $-CH_2C(O)NH_2$, $-OCH_3$, $-NH_2$ or $-NHCH_2CH_3$,
X–X' is $-CH_2-CH_2-$, $-CH=CH-$ or $-CH_2-C(O)-$; and
Y–Y' is $-CH_2-CH_2-$, $-CH=CH-$ or $-CH_2-C(O)-$; or X–X' is $-CH_2-$ and Y–Y' is $-CH_2-CH_2-C(O)-$;
wherein when one of X–X' and Y–Y' is $-CH_2-CH_2-$ and the other is $-CH=CH-$, or when both of X–X' and Y–Y' are $-CH=CH-$, then $R^2$ is $-S(O)_2CH_3$ or $-C(O)R^6$; or when X–X' and Y–Y' are $-CH_2-C(O)-$ then $R^2$ is hydrogen, $(C_1-C_3)$-alkyl, $-CH_2C(O)NH_2$ or $-CH(CH_3)C(O)NH_2$;
or a pharmaceutically acceptable salt thereof.

The invention comprises individual configurational isomers of the compounds herein as well as racemic and non-racemic mixtures thereof.

The compounds of the invention are selective inhibitors of monoamine oxidase B. As such, they are useful for the treatment of diseases in which the activity of monoamine oxidase B plays a role or is implicated. Such diseases include diseases of the central nervous system, such as Alzheimer's disease and senile dementia.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an" and "the" include plural forms unless the context clearly dictates otherwise.

The term "halogen" denotes fluorine, chlorine, bromine and iodine.

The term "$(C_1-C_3)$-alkyl" as used herein denotes straight-chain or branched saturated hydrocarbon residues with 1 to 3 carbon atoms. Examples for $(C_1-C_3)$-alkyl are methyl, ethyl, n-propyl and i-propyl. The $(C_1-C_3)$-alkyl can be unsubstituted or substituted by halogen. Examples for substituted $(C_1-C_3)$-alkyl include trifluoromethyl.

Examples for substituted phenyl include 3-fluoro-phenyl, 3-chloro-phenyl, 2,6-difluorophenyl and 2,3,4-trifluorophenyl.

"Pharmaceutically acceptable" such as pharmaceutically acceptable carrier, excipient, etc., means pharmacologically acceptable and substantially non-toxic to the subject to which the particular compound is administered.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid. If possible, compounds of formula I can be converted into pharmaceutically acceptable salts.

It should be understood that all references to pharmaceutically acceptable salts include solvent addition forms (solvates) or crystal forms (polymorphs) of the same acid addition salt.

Examples for pharmaceutically acceptable acid addition salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluene-sulfonic acid, trimethylacetic acid, trifluoroacetic acid, and the like.

"Monoamine oxidase B inhibiting amount" is the amount that is effective to reduce the amount of monoamine oxidase B in the patient.

"Therapeutically effective amount" means an amount that is effective to prevent, alleviate or ameliorate symptoms of disease or prolong the survival of the subject being treated.

"A mammal in need of treatment of an acute and/or chronic neurological disorder" means a mammal, e.g. a human, that is suffering from, or is at risk of suffering from, an acute and/or chronic neurological disorder.

The terms "treat, treating and treatment," and the like, as applied to an acute and/or chronic neurological disorder, refer to methods that slow, ameliorate, reduce or reverse such a disorder or any symptoms associated with said disorder, as currently afflicting the subject.

In a first aspect the present invention provides a compound of formula I

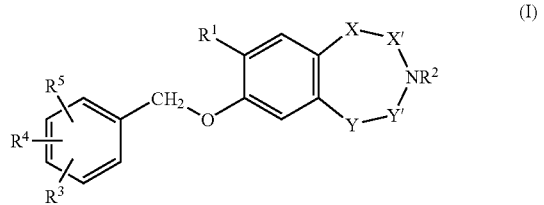

(I)

wherein
$R^1$ is hydrogen or methyl;
$R^2$ is hydrogen, $(C_1-C_3)$-alkyl, —$CH_2C(O)NH_2$, —$CH(CH_3)C(O)NH_2$, —$S(O)_2CH_3$ or —$C(O)R^6$;
$R^3$, $R^4$ and $R^5$ are each independently hydrogen, halogen, cyano, $(C_1-C_3)$-alkyl or —O—$(C_1-C_3)$-alkyl;
$R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$,
X–X' is —$CH_2$—$CH_2$—, —CH=CH— or —$CH_2$—C(O)—; and
Y–Y' is —$CH_2$—$CH_2$—, —CH=CH— or —$CH_2$—C(O)—; or
X–X' is —$CH_2$— and Y–Y' is —$CH_2$—$CH_2$—C(O)—;
wherein when one of X–X' and Y–Y' is —$CH_2$—$CH_2$— and the other is —CH=CH—, or when both of X–X' and Y–Y' are —CH=CH—, then $R^2$ is —$S(O)_2CH_3$ or —$C(O)R^6$; or when X–X' and Y–Y' are —$CH_2$—C(O)— then $R^2$ is hydrogen, $(C_1-C_3)$-alkyl, —$CH_2C(O)NH_2$ or —$CH(CH_3)C(O)NH_2$;
or a pharmaceutically acceptable salt thereof.

In one embodiment the present invention provides a compound of formula I, wherein $R^1$ is hydrogen.

In one embodiment the present invention provides a compound of formula I wherein $R^2$ is hydrogen. In another embodiment the present invention provides a compound of formula I wherein $R^2$ is —$CH_3$, —$CH_2C(O)NH_2$, —$CH(CH_3)C(O)NH_2$, —$S(O)_2CH_3$ or —$C(O)R^6$, wherein $R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$. In another embodiment the present invention provides a compound of formula I wherein $R^2$ is —$CH_3$, —$CH_2C(O)NH_2$ or —$CH(CH_3)C(O)NH_2$. In another embodiment the present invention provides a compound of formula I wherein $R^2$ is —$S(O)_2CH_3$ or —$C(O)R^6$, wherein $R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$.

In one embodiment the present invention provides a compound of formula I wherein $R^3$, $R^4$ and $R^5$ are each independently hydrogen or halogen. In still another embodiment the present invention provides a compound of formula I wherein $R^3$, $R^4$ and $R^5$ are hydrogen. In still another embodiment the present invention provides a compound of formula I wherein $R^3$, $R^4$ and $R^5$ are fluorine. In still another embodiment the present invention provides a compound of formula I wherein $R^3$ and $R^4$ are hydrogen and $R^5$ is fluorine. In still another embodiment the present invention provides a compound of formula I wherein $R^3$ is hydrogen and $R^4$ and $R^5$ are fluorine.

In one embodiment the present invention provides a compound of formula I wherein X–X' is —$CH_2$—$CH_2$— and Y–Y' is —$CH_2$—$CH_2$—. In another embodiment the present invention provides a compound of formula I wherein X–X' is —$CH_2$—$CH_2$— and Y–Y' is —$CH_2$—C(O)—. In still another embodiment the present invention provides a compound of formula I wherein X–X' is —CH=CH— and Y–Y' is —$CH_2$—C(O)—. In still another embodiment the present invention provides a compound of formula I wherein X–X' is —$CH_2$—C(O)— and Y–Y' is —$CH_2$—$CH_2$—. In still another embodiment the present invention provides a compound of formula I wherein X–X' is —$CH_2$—C(O)—; and Y–Y' is —CH=CH—. In still another embodiment the present invention provides a compound of formula I wherein X–X' is —$CH_2$— and Y–Y' is —$CH_2$—$CH_2$—C(O)—.

In one embodiment the present invention provides a compound of formula I wherein
$R^1$ is hydrogen;
$R^2$ is hydrogen, —$CH_3$, —$CH_2C(O)NH_2$, —$CH(CH_3)C(O)NH_2$, —$S(O)_2CH_3$ or —$C(O)R^6$;
$R^3$, $R^4$ and $R^5$ are each independently hydrogen, halogen, cyano, $(C_1-C_3)$-alkyl or —O—$(C_1-C_3)$-alkyl;

$R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$, X–X' is —$CH_2$—$CH_2$—, —CH=CH— or —$CH_2$—C(O)—; and Y–Y' is —$CH_2$—$CH_2$—, —CH=CH— or —$CH_2$—C(O)—; or X–X' is —$CH_2$— and Y–Y' is —$CH_2$—$CH_2$—C(O)—;

wherein when one of X–X' and Y–Y' is —$CH_2$—$CH_2$— and the other is —CH=CH—, or when both of X–X' and Y–Y' are —CH=CH—, then $R^2$ is —$S(O)_2CH_3$ or —$C(O)R^6$; or when X–X' and Y–Y' are —$CH_2$—C(O)— then $R^2$ is hydrogen, ($C_1$–$C_3$)-alkyl, —$CH_2C(O)NH_2$ or —$CH(CH_3)C(O)NH_2$.

In another embodiment the present invention provides a compound of formula I wherein $R^1$ is hydrogen;

$R^2$ is hydrogen, —$CH_3$, —$CH_2C(O)NH_2$, —$CH(CH_3)C(O)NH_2$, —$S(O)_2CH_3$ or —$C(O)R^6$;

$R^3$, $R^4$ and $R^5$ are each independently hydrogen, halogen, cyano, ($C_1$–$C_3$)-alkyl or —O—($C_1$–$C_3$)-alkyl;

$R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$, X–X' and Y–Y' are —$CH_2$—$CH_2$—.

In another embodiment the present invention provides a compound of formula I wherein $R^1$ is hydrogen;

$R^2$ is —$CH_2C(O)NH_2$, —$CH(CH_3)C(O)NH_2$, —$S(O)_2CH_3$ or —$C(O)R^6$;

$R^3$ is halogen and $R^4$ and $R^5$ are each independently hydrogen or halogen;

$R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$, X–X' and Y–Y' are —$CH_2$—$CH_2$—.

In another embodiment the present invention provides a compound of formula I wherein $R^1$ is hydrogen;

$R^2$ is hydrogen, —$CH_3$, —$CH_2C(O)NH_2$, —$CH(CH_3)C(O)NH_2$, —$S(O)_2CH_3$ or —$C(O)R^6$;

$R^3$, $R^4$ and $R^5$ are each independently hydrogen, halogen, cyano, ($C_1$–$C_3$)-alkyl or —O—($C_1$–$C_3$)-alkyl;

$R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$, X–X' is —CH=CH— and Y–Y' is —$CH_2$—C(O)—.

In another embodiment the present invention provides a compound of formula I wherein $R^1$ is hydrogen;

$R^2$ is hydrogen, —$CH_3$ or —$C(O)R^6$;

$R^3$ is halogen and $R^4$ and $R^5$ are each independently hydrogen or halogen;

$R^6$ is —$CH_3$ or —$CH_2OCH_3$;

X–X' is —CH=CH— and Y–Y' is —$CH_2$—C(O)—.

In another embodiment the present invention provides a compound of formula I wherein $R^1$ is hydrogen;

$R^2$ is hydrogen, —$CH_3$, —$CH_2C(O)NH_2$, —$CH(CH_3)C(O)NH_2$, —$S(O)_2CH_3$ or —$C(O)R^6$;

$R^3$, $R^4$ and $R^5$ are each independently hydrogen, halogen, cyano, ($C_1$–$C_3$)-alkyl or —O—($C_1$–$C_3$)-alkyl;

$R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$, X–X' is —$CH_2$—$CH_2$— and Y–Y' is —$CH_2$—C(O)—.

In another embodiment the present invention provides a compound of formula I wherein $R^1$ is hydrogen;

$R^2$ is hydrogen;

$R^3$ is halogen and $R^4$ and $R^5$ are each independently hydrogen or halogen;

X–X' is —$CH_2$—$CH_2$— and Y–Y' is —$CH_2$—C(O)—.

In another embodiment the present invention provides a compound of formula I wherein $R^1$ is hydrogen;

$R^2$ is hydrogen, —$CH_3$, —$CH_2C(O)NH_2$, —$CH(CH_3)C(O)NH_2$, —$S(O)_2CH_3$ or —$C(O)R^6$;

$R^3$, $R^4$ and $R^5$ are each independently hydrogen, halogen, cyano, ($C_1$–$C_3$)-alkyl or —O—($C_1$–$C_3$)-alkyl;

$R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$, X–X' is —$CH_2$—C(O)— and Y–Y' is —$CH_2$—$CH_2$—.

In another embodiment the present invention provides a compound of formula I wherein $R^1$ is hydrogen;

$R^2$ is hydrogen or —$C(O)R^6$;

$R^3$, $R^4$ and $R^5$ are each independently hydrogen or halogen;

$R^6$ is —$CH_3$;

X–X' is —$CH_2$—C(O)— and Y–Y' is —$CH_2$—$CH_2$—.

In another embodiment the present invention provides a compound of formula I wherein $R^1$ is hydrogen;

$R^2$ is hydrogen, —$CH_3$, —$CH_2C(O)NH_2$, —$CH(CH_3)C(O)NH_2$, —$S(O)_2CH_3$ or —$C(O)R^6$;

$R^3$, $R^4$ and $R^5$ are each independently hydrogen, halogen, cyano, ($C_1$–$C_3$)-alkyl or —O—($C_1$–$C_3$)-alkyl;

$R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$, X–X' is —$CH_2$— and Y–Y' is —$CH_2$—$CH_2$—C(O)—.

In another embodiment the present invention provides a compound of formula I wherein $R^1$ is hydrogen;

$R^2$ is hydrogen;

$R^3$ is halogen and $R^4$ and $R^5$ are each independently hydrogen or halogen;

X–X' is —$CH_2$— and Y–Y' is —$CH_2$—$CH_2$—C(O)—.

In one embodiment the present invention provides a compound of formula I selected from 1-[7-(3-fluoro-benzyloxy)-1,2,4,5-tetrahydro-benzo[d] azepin-3-yl]-ethanone, 1-[7-(3-fluoro-benzyloxy)-1,2,4,5-tetrahydro-benzo[d] azepin-3-yl]-2-methoxy-ethanone, 2-[7-(3-fluoro-benzyloxy)-1,2,4,5-tetrahydro-benzo[d] azepin-3-yl]-2-oxo-acetamide, 3-[7-(3-fluoro-benzyloxy)-1,2,4,5-tetrahydro-benzo[d] azepin-3-yl]-3-oxo-propionamide, 7-(3-fluoro-benzyloxy)-1,2,4,5-tetrahydro-benzo[d] azepine-3-carboxylic acid methyl ester, 7-(3-fluoro-benzyloxy)-1,2,4,5-tetrahydro-benzo[d] azepine-3-carbaldehyde, 7-(3-fluoro-benzyloxy)-3-methanesulfonyl-2,3,4,5-tetrahydro-1H-benzo[d]azepine, 7-(3-fluoro-benzyloxy)-1,2,4,5-tetrahydro-benzo[d] azepine-3-carboxylic acid amide, 7-(3-fluoro-benzyloxy)-1,2,4,5-tetrahydro-benzo[d] azepine-3-carboxylic acid ethylamide, 2-[7-(3-fluoro-benzyloxy)-1,2,4,5-tetrahydro-benzo[d] azepin-3-yl]-acetamide, (RS)-2-[7-(3-fluoro-benzyloxy)-1,2,4,5-tetrahydro-benzo[d]azepin-3-yl]-propionamide, 8-(3-fluoro-benzyloxy)-1,3-dihydro-benzo[d]azepin-2-one, 8-(3-fluoro-benzyloxy)-3-methyl-1,3-dihydro-benzo[d] azepin-2-one, 8-(3-fluoro-benzyloxy)-3-methoxyacetyl-1,3-dihydro-benzo[d]azepin-2-one 3-acetyl-8-(3-fluoro-benzyloxy)-1,3-dihydro-benzo[d] azepin-2-one, 8-(3-fluoro-benzyloxy)-1,3,4,5-tetrahydro-benzo[d]azepin-2-one,
7-(2,3,4-trifluoro-benzyloxy)-1,3,4,5-tetrahydro-benzo[d]azepin-2-one,
7-(2,3,4-trifluoro-benzyloxy)-1,2,4,5-tetrahydro-benzo[c]azepin-3-one,
7-(2,6-difluoro-benzyloxy)-1,3,4,5-tetrahydro-benzo[d]azepin-2-one,
7-(2,6-difluoro-benzyloxy)-1,2,4,5-tetrahydro-benzo[c]azepin-3-one,
7-benzyloxy-1,3,4,5-tetrahydro-benzo[d]azepin-2-one,
7-(3-fluoro-benzyloxy)-1,3,4,5-tetrahydro-benzo[d]azepin-2-one,
7-(3-chloro-benzyloxy)-1,3,4,5-tetrahydro-benzo[d]azepin-2-one,
3-acetyl-7-(3-chloro-benzyloxy)-1,3,4,5-tetrahydro-benzo[d]azepin-2-one and
7-(3-fluoro-benzyloxy)-1,2,4,5-tetrahydro-benzo[c]azepin-2-one.

In another aspect the present invention provides a process for the preparation of a compound of formula I wherein
$R^1$ is hydrogen or methyl;
$R^2$ is hydrogen;
$R^3$, $R^4$ and $R^5$ are each independently hydrogen, halogen, cyano, $(C_1-C_3)$-alkyl or —O—$(C_1-C_3)$-alkyl;
X–X' is —$CH_2$—$CH_2$—, —CH=CH— or —$CH_2$—C(O)—; and
Y–Y' is —$CH_2$—$CH_2$—, —CH=CH— or —$CH_2$—C(O)—; or
X–X' is —$CH_2$— and Y–Y' is —$CH_2$—$CH_2$—C(O)—;
wherein when one of X–X' and Y–Y' is —$CH_2$—$CH_2$— and the other is —CH=CH—, or when both of X–X' and Y–Y' are —CH=CH—, then $R^2$ is —$S(O)_2CH_3$ or —$C(O)R^6$; or when X–X' and Y–Y' are —$CH_2$—C(O)— then $R^2$ is hydrogen, $(C_1-C_3)$-alkyl, —$CH_2C(O)NH_2$ or —$CH(CH_3)C(O)NH_2$;
which comprises cleaving a protecting group from a compound of formula II

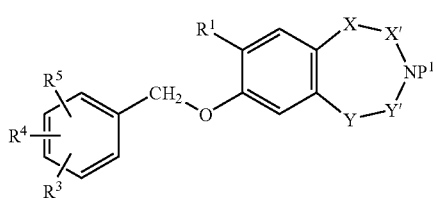

(II)

wherein $P^1$ is a protecting group like, e.g. a tert-butoxycarbonyl, a methoxycarbonyl or 9-fluorenyl-methoxycarbonyl group.

In another aspect the present invention provides a process for the preparation of a compound of formula I wherein
$R^1$ is hydrogen or methyl;
$R^2$ is hydrogen, $(C_1-C_3)$-alkyl, —$CH_2C(O)NH_2$, —$CH(CH_3)C(O)NH_2$, —$S(O)_2CH_3$ or —$C(O)R^6$;
$R^3$, $R^4$ and $R^5$ are each independently hydrogen, halogen, cyano, $(C_1-C_3)$-alkyl or —O—$(C_1-C_3)$-alkyl;
$R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$,
X–X' is —$CH_2$—$CH_2$—, —CH=CH— or —$CH_2$—C(O)—; and
Y–Y' is —$CH_2$—$CH_2$—, —CH=CH— or —$CH_2$—C(O)—; or
X–X' is —$CH_2$— and Y–Y' is —$CH_2$—$CH_2$—C(O)—;
wherein when one of X–X' and Y–Y' is —$CH_2$—$CH_2$— and the other is —CH=CH—, or when both of X–X' and Y–Y' are —CH=CH—, then $R^3$ is —$S(O)_2CH_3$ or —$C(O)R^5$; or when X–X' and Y–Y' are —$CH_2$—C(O)— then $R^3$ is hydrogen, $(C_1-C_3)$-alkyl, —$CH_2C(O)NH_2$ or —$CH(CH_3)C(O)NH_2$;
which comprises reacting a compound of formula III

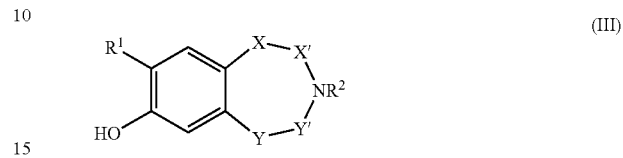

(III)

with a compound of formula IV

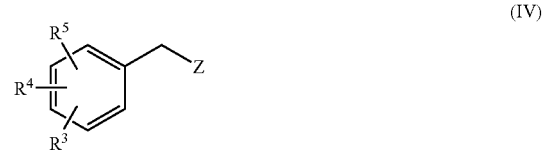

(IV)

wherein Z is OH, or, when $R^2$ is —$S(O)_2CH_3$ or —$C(O)R^6$, then Z can also be halogen or a sulfonic acid residue.

In another aspect the present invention provides a process for the preparation of a compound of formula I wherein
$R^1$ is hydrogen or methyl;
$R^2$ is —$S(O)_2CH_3$ or —$C(O)R^6$;
$R^3$, $R^4$ and $R^5$ are each independently hydrogen, halogen, cyano, $(C_1-C_3)$-alkyl or —O—$(C_1-C_3)$-alkyl;
$R^6$ is hydrogen, —$CH_3$, —$CH_2OCH_3$, —$OCH_3$, —$NH_2$ or —$NHCH_2CH_3$,
X–X' is —$CH_2$—$CH_2$—, —CH=CH— or —$CH_2$—C(O)—; and
Y–Y' is —$CH_2$—$CH_2$—, —CH=CH— or —$CH_2$—C(O)—; or
X–X' is —$CH_2$— and Y–Y' is —$CH_2$—$CH_2$—C(O)—;
wherein X–X' and Y–Y' are not —$CH_2$—C(O)— at the same time;
which comprises reacting a compound of formula I wherein $R^2$ is hydrogen, with an activated acyl derivative; or by a condensation reaction of an acid using a condensation reagent; or by reaction with an activated sulfonyl derivative; or by reaction with an isocyanate.

Examples for an activated acyl derivative include acyl halogenides and anhydrides as well as chloroformates.

Examples for an activated sulfonyl derivative include sulfonyl halogenides and anhydrides.

Examples for a condensation reagent include carbodiimides.

In another aspect the present invention provides a process for the preparation of a compound of formula I wherein
$R^1$ is hydrogen or methyl;
R is —$S(O)_2CH_3$ or —$C(O)R^6$;
$R^3$, $R^4$ and $R^5$ are each independently hydrogen, halogen, cyano, $(C_1-C_3)$-alkyl or —O—$(C_1-C_3)$-alkyl;
$R^6$ is —$C(O)NH_2$ or —$CH_2C(O)NH_2$,
X–X' is —$CH_2$—$CH_2$—, —CH=CH— or —$CH_2$—C(O)—; and
Y–Y' is —$CH_2$—$CH_2$—, —CH=CH— or —$CH_2$—C(O)—; or X–X' is —CH$_2$— and Y–Y' is —CH$_2$—CH$_2$—C(O)—;
wherein X–X' and Y–Y' are not —CH$_2$—C(O)— at the same time;

which comprises reacting a compound of formula I wherein R$^2$ is hydrogen, with an activated acyl derivative; or by a condensation reaction of an acid using a condensation reagent; and converting the resulting ester function into a corresponding amide.

In another aspect the present invention provides a process for the preparation of a compound of formula I wherein
R$^1$ is hydrogen or methyl;
R$^2$ is (C$_1$–C$_3$)-alkyl, —CH$_2$C(O)NH$_2$ or —CH(CH$_3$)C(O)NH$_2$;
R$^3$, R$^4$ and R$^5$ are each independently hydrogen, halogen, cyano, (C$_1$–C$_3$)-alkyl or —O—(C$_1$–C$_3$)-alkyl;
X–X' is —CH$_2$—CH$_2$—, —CH=CH— or —CH$_2$—C(O)—; and
Y–Y' is —CH$_2$—CH$_2$—, —CH=CH— or —CH$_2$—C(O)—; or
X–X' is —CH$_2$— and Y–Y' is —CH$_2$—CH$_2$—C(O)—;
wherein X–X' and Y–Y' are not —CH=CH— at the same time, or X–X' and Y–Y' are not —CH$_2$—CH$_2$— when the other is —CH=CH—;

which comprises reacting a compound of formula I wherein R$^2$ is hydrogen, with an alkylating agent.

Examples for alkylating agents include halides, tosylates, mesylates and triflates.

In accordance with the present invention, compounds of general formula I wherein X–X' and Y–Y' are —CH$_2$—CH$_2$— can, e.g., be manufactured in the following manner: With the benzazepine derivative V [J. Heterocycl. Chem. (1971) 8(5), 779–783] as starting material, compounds of formula I, wherein R$^2$ is hydrogen and X–X' and Y–Y' are —CH$_2$—CH$_2$—, can be obtained using suitably protected benzazepine derivatives of formula VI. As amino protecting groups P$^1$ can be selected those, that can be cleaved in the presence of the benzyl residue to be introduced in the following step, e.g. tert-butoxycarbonyl, methoxycarbonyl, or 9-fluorenyl-methoxycarbonyl.

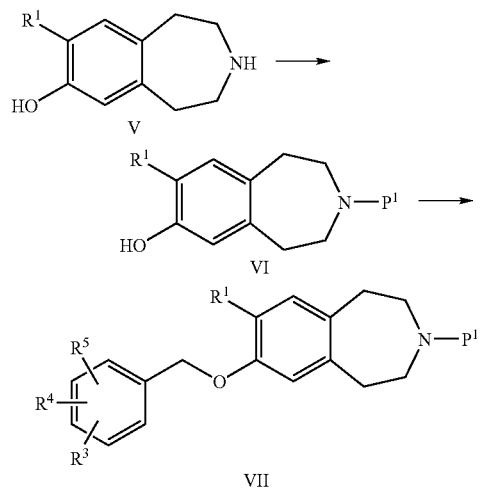

The alkylation of the phenol VI is effected according to methods which are known per se in the presence of a base, such as potassium carbonate or cesium carbonate. Chlorides, bromides, iodides, tosylates or mesylates can be used as alkylating agents. The reaction is effected in a solvent which is inert under the reaction conditions, such as e.g. acetone, methyl ethyl ketone, or N,N-dimethylformamide, at a temperature between about 0° C. and 140° C. As an alternative approach, the Mitsunobu reaction of optionally substituted benzylalcohols in inert solvents, such as e.g. diethyl ether or tetrahydrofurane, using dialkyl-azo-dicarboxylates, e.g. diethyl or diisopropyl-azo-dicarboxylates, in the presence of phosphines, such as e.g. triphenyl- or tributylphosphine, leads to ethers of formula VII. Especially in benzyl derivatives of formula VII with R$^3$, R$^4$ and R$^5$=hydrogen, the benzyl group can be used as a protecting group and, after its cleavage by hydrogenolysis, be replaced at a later stage by differently substituted benzyl groups using methods mentioned before.

For the preparation of amines of formula I, i.e. wherein R$^2$ is hydrogen, the protecting group has to be cleaved in an appropriate way depending on the nature of P$^1$ generally known to those skilled in the art, e.g. by cleavage under acidic conditions in case of the tert-butoxycarbonyl group, or under basic conditions in case of the methoxycarbonyl- or 9-fluorenyl-methoxycarbonyl group.

The derivatisation of compounds of formula I wherein R$^2$ is hydrogen can lead directly to compounds of formula I wherein R$^2$ is (C$_1$–C$_3$)-alkyl, —CH$_2$C(O)NH$_2$, —CH(CH$_3$)C(O)NH$_2$, —S(O)$_2$CH$_3$ or —C(O)R$^6$. When R is an acyl residue, activated acid derivatives, such as e.g. an acid chloride or anhydride, can be used, or condensation methods for acids and amines known per se can be applied. When R$^2$ is an alkoxycarbonyl residue, chloroformates can be used. When R$^2$ is an aminocarbonyl residue, isocyanates, e.g. trimethylsilyl-isocyanate or alkyl-isocyanates, can be used. When R$^2$ is a sulfonyl residue, activated derivatives, such as e.g. a sulfonyl chloride or anhydride, can be used. When R$^2$ is representing an alkyl residue, the alkylation is effected according to methods which are known per se in the presence of a base, such as potassium carbonate or cesium carbonate with chlorides, bromides, iodides, tosylates or mesylates as the alkylating agent. The reaction is effected in a solvent which is inert under the reaction conditions, such as e.g. acetone, methyl ethyl ketone, or N,N-dimethylformamide, at a temperature between about 0° C. and 140° C.

The derivatisation of compounds of formula I wherein R$^2$ is hydrogen can also be achieved via compounds of formula IX, wherein R$^{2.1}$ contains a functional group that can be transformed in R$^2$, such as e.g. an alkyl ester which by ammonolysis is transformed into the corresponding amide.

Compounds of formula IX can be obtained directly via compounds of formula VIII where R$^{2.1}$ represents an acyl, alkoxycarbonyl, or sulfonyl residue. Compounds of formula VIII can be prepared using procedures as described before in the case of the derivatisation of compounds of formula I wherein R$^2$ is hydrogen.

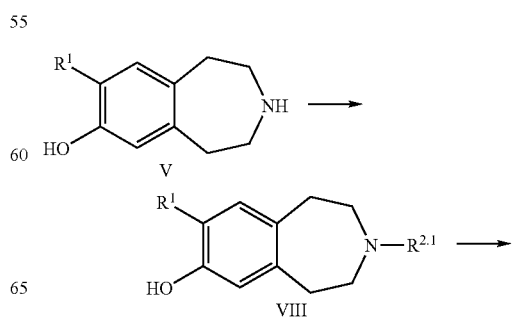

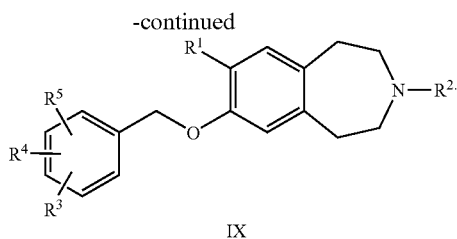

IX

Compounds of formula I wherein X–X' is —CH═CH— and Y–Y' is —CH$_2$—C(O)— can be obtained as outlined as follows via the intermediate 8-hydroxy-1,3-dihydrobenzo[d] azepin-2-one (XII) and procedures known from the literature or in close analogy thereof, e.g. as described in J. Med. Chem. 33 (5) 1496–1504 (1990).

Starting with the condensation of activated derivatives of 3-hydroxyphenylacetic acid wherein R$^9$ has the meaning of methyl or benzyl [Synthesis 9, 1214–1216 (2000)], the reaction with aminoacetaldehyde acetal, wherein R$^{10}$ has the meaning of e.g. methyl or ethyl, leads to amide XI. The ring closure to the seven-membered cycle can be performed under acid conditions, such as e.g. concentrated hydrochloric acid in acetic acid or polyphosphorous acid, under, at least partial, loss of group R$^9$ to yield the azepinone XII.

The further derivatisation to compounds of formula I follows procedures already described above.

When R$^2$ is an acyl, alkoxycarbonyl, or sulfonyl residue, compounds of formula I can be obtained following procedures already described above. When R$^2$ is alkyl, the alkylation is effected according to methods known per se in the presence of a base, such as e.g. alcoholates, like potassium tert-butanolate, or hydride, like sodium hydride, with chlorides, bromides, iodides, tosylates or mesylates as the alkylating agent and in solvents such as e.g. dimethylsulfoxide, N,N-dimethylformamide or THF.

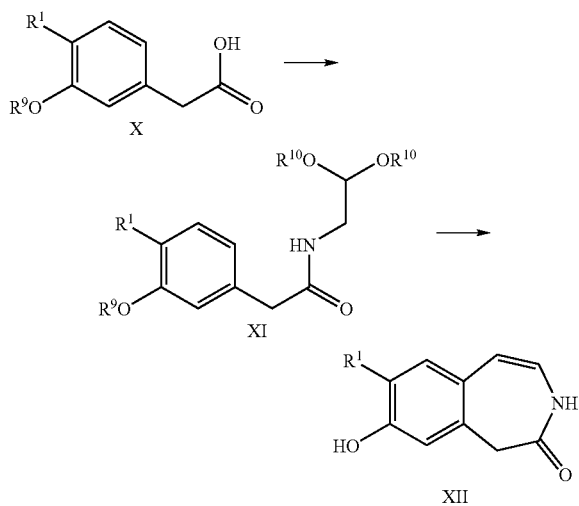

Compounds of formula I wherein X–X' is —CH$_2$—CH$_2$— and Y–Y' is —CH$_2$C(O)— can be obtained via the intermediate XIII by methods described above. The azepinone XIII can be obtained by hydrogenation of XII.

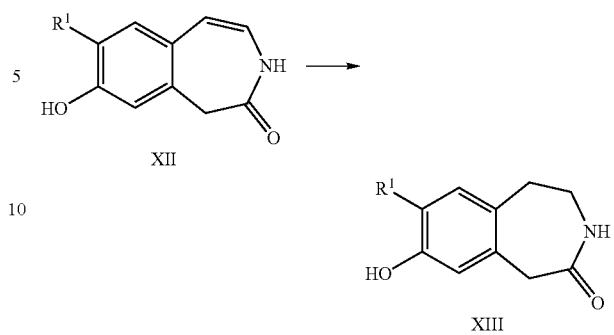

Compounds of formula I wherein X–X' is —CH$_2$C(O)— and Y–Y' is —CH═CH— can be prepared starting from intermediates of formula XVI or XVI-1 as outlined as follows by methods already described above.

The intermediate azepinone XVI can be obtained in different ways:

(a) Following a procedure, described in Heterocycles 9 (9), 1197 (1978) for the synthesis of the corresponding six-membered cycle, acylation of phenethylamine XIV by dialkoxy-acetyl chloride yields the dialkoxy-acetamide XV which is cyclised to the azepinone XVI by acid, such as e.g. concentrated sulfuric acid. Herein, R$^{10}$ can have the meaning of methyl or benzyl, representing transient groups which, at least partially, can be lost during the cyclisation procedure.

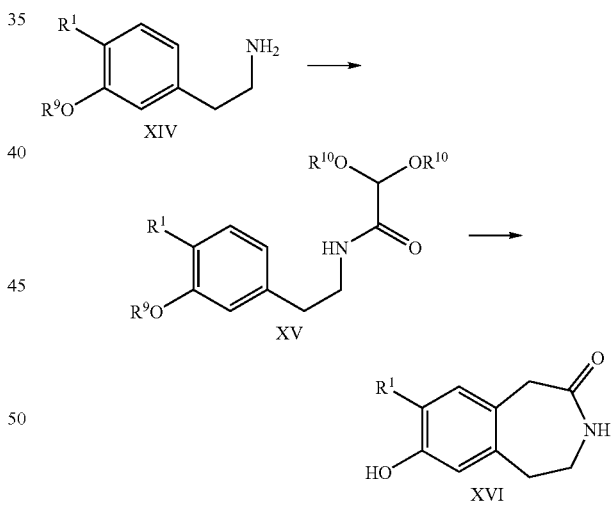

(b) Alternatively, following the procedure described in Chem. Pharm. Bull. 37 (4) 939–943 (1989), the cyclisation to the azepinone XVI can be performed by a Pummerer-type reaction, via the sulfide XVIII, its oxidation, e.g. by sodium metaperiodate, to the α-(methylsulfinyl)acetamide XX (R$^{11}$=methyl) and cyclisation to the azepinone XX by acid treatment, e.g. 4-toluenesulfonic acid, or by treatment with trifluoroacetic anhydride. The desulfurisation of XX by Raney nickel yields azepinone XXI or XVI depending on the protecting group P$^2$. P$^2$ can represent a typical amino protecting group, such as e.g. tert-butoxycarbonyl or benzyloxycarbonyl.

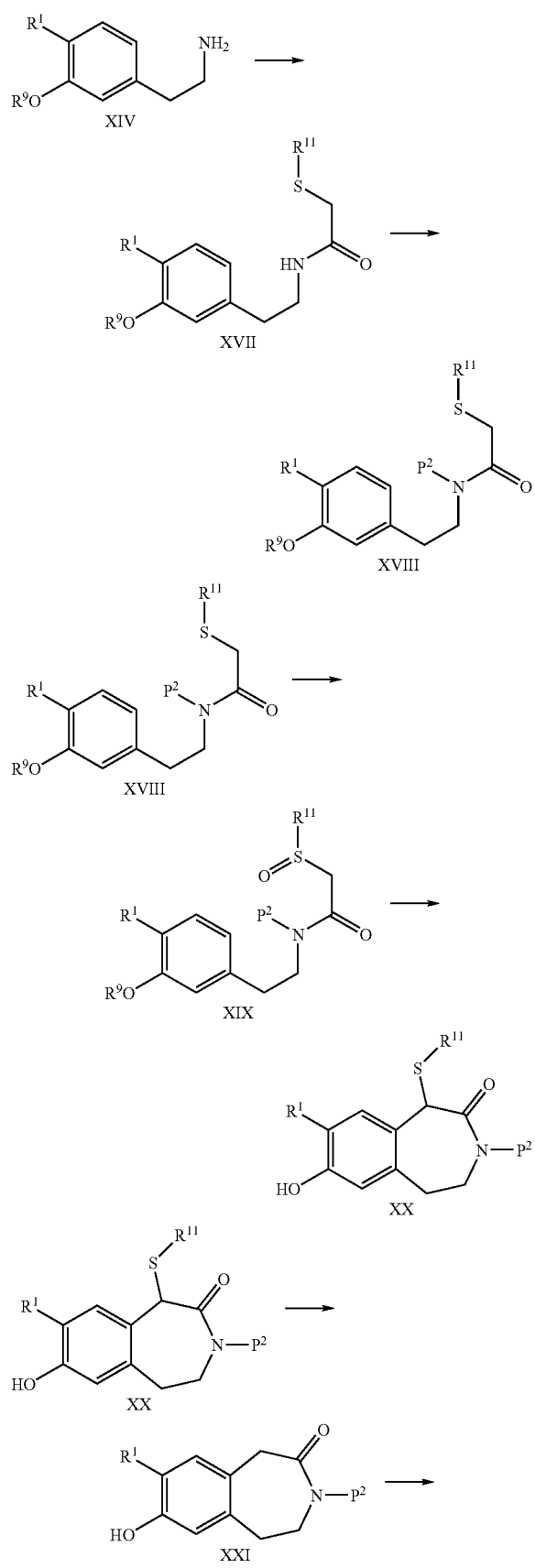

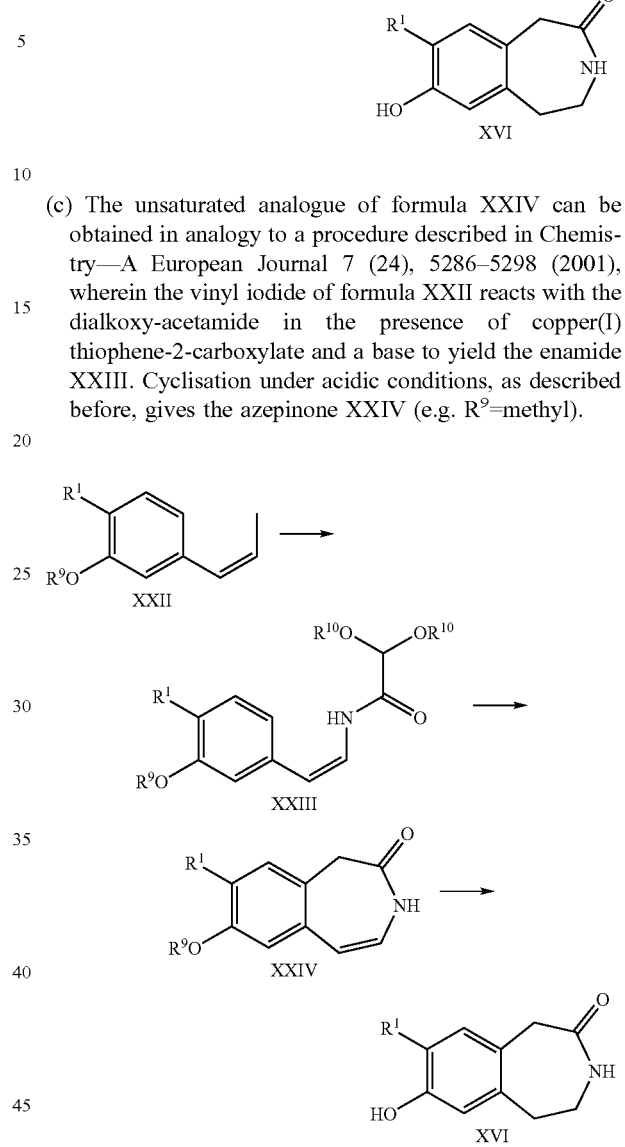

(c) The unsaturated analogue of formula XXIV can be obtained in analogy to a procedure described in Chemistry—A European Journal 7 (24), 5286–5298 (2001), wherein the vinyl iodide of formula XXII reacts with the dialkoxy-acetamide in the presence of copper(I) thiophene-2-carboxylate and a base to yield the enamide XXIII. Cyclisation under acidic conditions, as described before, gives the azepinone XXIV (e.g. $R^9$=methyl).

The compound of formula XXII can be prepared starting from the corresponding alpha,beta-unsaturated aromatic carboxylic acids by oxidative halodecarboxylation as described e.g. in Tetrahedron Letters 42 (52) 9253 (2001), followed by transhalogenation to the corresponding iodide as described in e.g. Synthesis (3), 236–238 (1988).

Ring expansion reactions as known to those skilled in the art can lead to compounds of formula XXX and XVI-1. Examples of such reactions are outlined as follows, like e.g. the Schmidt rearrangement or the Beckmann rearrangement, both starting, e.g., from the commercially available 6-methoxy-2-tetralone (XXV).

Treatment of XXV with hydrazoic acid yields a mixture of azepinones of formula XXX and XVI-1 which, after separation, can be transformed to compounds of general formula XIII or I, respectively. The separation can also take place at a later stage of the synthesis.

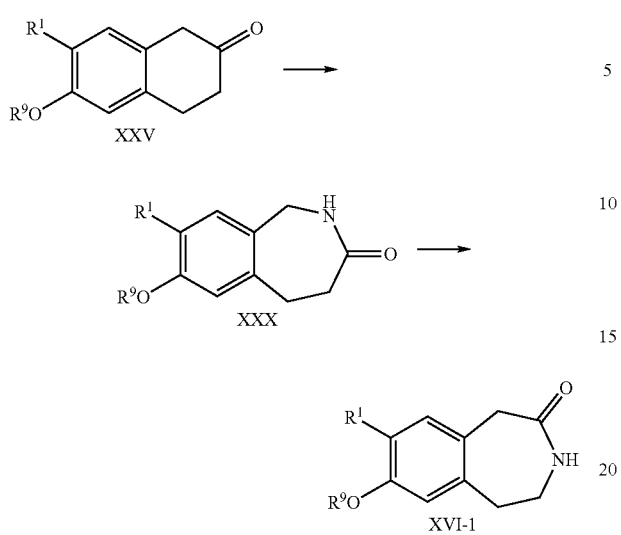

In an analogous manner, via the oxime XXVI by its rearrangement after treatment with reagents such as e.g. phosphorous pentachloride, sulfuric acid or polyphosphoric acid, a mixture of azepinones of formula XXX and XVI-1 can be obtained.

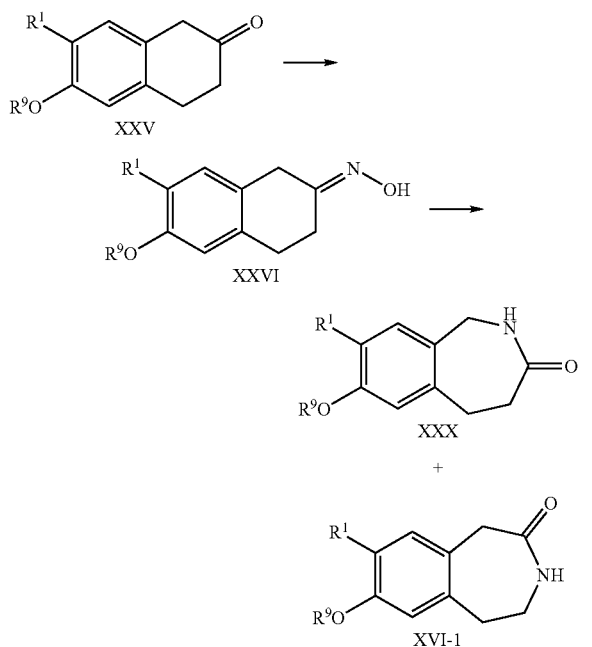

Another approach to obtain azepinones of formula XVI-1 is given by the oxidative ring expansion of an isoquinoline enamide of formula XXVII [compound of formula XXVII can be prepared as described in: Tetrahedron Letters 43 (29) 5089–5091 (2002) for $R^9$=methyl or as described in Bioorg. Med. Chem. Lett. 13 (17), 2853 (2003)] by lead tetraacetate as described in J.Org.Chem. 53, 5793–5796 (1988).

Pharmaceutically acceptable salts of compounds of formula I can be manufactured readily according to methods known per se and taking into consideration the nature of the compound to be converted into a salt. Inorganic or organic acids such as, e.g., hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I.

The following examples are provided to illustrate the preparation of some examples for compounds of formula I. They should not be considered as limiting the scope of the invention, but merely as being representative thereof. The term "room temperature" was abbreviated as "RT".

EXAMPLE 1

1-[7-(3-Fluoro-benzyloxy)-1,2,4,5-tetrahydro-benzo[d]azepin-3-yl]-ethanone a) 7-Hydroxy-1,2,4,5-tetrahydro-benzo[d]azepine-3-carboxylic acid tert-butyl ester: The white suspension of 2.3 g (14.1 mmol) of 2,3,4,5-tetrahydro-7-hydroxy-1H-3-benzazepine [J. Heterocycl. Chem. 8:779–783 (1971)] in a mixture of 40 ml of water and 80 ml of dioxane was treated at 0° C. successively with 4.48 g (42.3 mmol) of sodium carbonate and 6.27 g (28.2 mmol) of di-tert-butyl-dicarbonate. The mixture was left to warm to RT and stirred during 18 h. For the working-up, the mixture was treated with a saturated solution of ammoniumchloride and ethylacetate, thereupon, the aqueous layer was separated and washed twice with ethylacetate. The combined organic layers were dried over sodium sulfate, then the filtrate was evaporated under reduced pressure. For purification, the crude material obtained (6.21 g of a yellow oil) was chromatographed on silica gel using a 3:1 mixture of n-hexane and ethyl acetate as the eluent. There were obtained 2.81 g (76% of theory) of 7-hydroxy-1,2,4,5-tetrahydro-benzo[d]azepine-3-carboxylic acid tert-butyl ester as a white solid; MS: m/e=262 (M+H)$^+$.

b) 7-(3-Fluoro-benzyloxy)-1,2,4,5-tetrahydro-benzo[d]azepine-3-carboxylic acid tert-butyl ester: The suspension of 2.75 g (10.4 mmol) of 7-hydroxy-1,2,4,5-tetrahydro-benzo[d]azepine-3-carboxylic acid tert-butyl ester in 33 ml of acetone was successively treated with 1.56 g (11.5 mmol) of potassium carbonate in solid form and 1.48 ml (11.5 mmol) of 3-fluorobenzyl-bromide. The mixture was heated under reflux during 18 h. For the working-up, 1 g of silica gel was added to the cooled reaction mixture, which was then evaporated under reduced pressure. For purification, the residue obtained was chromatographed on silica gel by flash-chromatography using a 4:1-mixture of n-hexane and ethyl-acetate as the eluent. There were obtained 3.42 g (88% of theory) of 7-(3-fluoro-benzyloxy)-1,2,4,5-tetrahydro-benzo[d]azepine-3-carboxylic acid tert-butyl ester as a colourless oil; MS: m/e=371 (M+H)$^+$.

c) 7-(3-Fluoro-benzyloxy)-2,3,4,5-tetrahydro-1H-benzo[d]azepine hydrochloride: A solution of 3.18 g (8.6 mmol) of 7-(3-fluoro-benzyloxy)-1,2,4,5-tetrahydro-benzo[d]azepine-3-carboxylic acid tert-butyl ester in 47 ml methanol was treated with 6.8 ml (85.6 mmol) of hydrochloric acid (37%), and the yellowish solution was heated at 45° C. during 1 h. For the working-up, the reaction mixture was evaporated under reduced pressure to yield 2.42 g (92% of theory) of 7-(3-fluoro-benzyloxy)-2,3,4,5-tetrahydro-1H-benzo[d]azepine hydrochloride as a white solid which was used in the next step without further purification; MS: m/e=272 (M+H)$^+$.

d) 1-[7-(3-Fluoro-benzyloxy)-1,2,4,5-tetrahydro-benzo[d]azepin-3-yl]-ethanone: A solution of 50 mg (0.16 mmol) of 7-(3-fluoro-benzyloxy)-2,3,4,5-tetrahydro-1H-benzo[d]azepine hydrochloride in 1 ml dichloromethane was treated with 50 μl (0.36 mmol) of triethylamine. After cooling to 0° C., 13 μl (0.18 mmol) of acetylchloride were added to the solution, and stirring at 0° C. was continued for 30 min. For the working-up, 2 ml of a saturated aqueous solution of ammonium chloride were added, the organic layer was separated, dried over sodium sulfate and evaporated to yield 99 mg of crude material. For purification, the material was chromatographed on silica gel using a 98:2-mixture of dichloromethane and methanol as the eluent. There were obtained 44 mg (87% of theory) of 1-[7-(3-fluoro-benzyloxy)-1,2,4,5-tetrahydro-benzo[d]azepin-3-yl]-ethanone as a colourless oil; MS: m/e=313 (M)$^+$.

EXAMPLE 2

1-[7-(3-Fluoro-benzyloxy)-1,2,4,5-tetrahydro-benzo[d]azepin-3-yl]-2-methoxy-ethanone The title compound was prepared in analogy to Example 1 d) from 7-(3-fluoro-benzyloxy)-2,3,4,5-tetrahydro-1H-benzo[d]azepine hydrochloride [Example 1c)] and methoxy-acetic acid chloride with N-ethyl-diisopropylamine as the base. Yield: 98% of theory as a colourless oil; MS: m/e=344 (M+H)$^+$.

EXAMPLE 3

2-[7-(3-Fluoro-benzyloxy)-1,2,4,5-tetrahydro-benzo[d]azepin-3-yl]-2-oxo-acetamide a) [7-(3-Fluoro-benzyloxy)-1,2,4,5-tetrahydro-benzo[d]azepin-3-yl]-oxo-acetic acid ethyl ester: The title compound was prepared in analogy to Example 1d) from 7-(3-fluoro-benzyloxy)-2,3,4,5-tetrahydro-1H-benzo[d]azepine hydrochloride [Example 1c)] and ethyl oxalic acid chloride with triethylamine as the base. Yield: 88% of theory as a colourless oil; MS: m/e=372 (M+H)$^+$.

b) 2-[7-(3-Fluoro-benzyloxy)-1,2,4,5-tetrahydro-benzo[d]azepin-3-yl]-2-oxo-acetamide: In a sealed tube, a mixture of 52 mg (0.14 mmol) of [7-(3-fluoro-benzyloxy)-1,2,4,5-tetrahydro-benzo[d]azepin-3-yl]-oxo-acetic acid ethyl ester and 0.7 ml (4.6 mmol) of an aqueous ammonium hydroxide solution (25%) in 0.5 ml dioxane was heated at 100° C. during 2 h. For the working-up, the reaction mixture was evaporated under reduced pressure. The residue was purified by preparative HPLC using a gradient of a 95:5-mixture to a 5:95-mixture of water and acetonitrile (+0.1% of formic acid) as the eluent, and 43 mg (88% of theory) of 2-[7-(3-fluoro-benzyloxy)-1,2,4,5-tetrahydro-benzo[d]azepin-3-yl]-2-oxo-acetamide were obtained as a white solid; MS: m/e=360 (M+NH$_4$)$^+$.

EXAMPLE 4

3-[7-(3-Fluoro-benzyloxy)-1,2,4,5-tetrahydro-benzo[d]azepin-3-yl]-3-oxo-propionamide a) 3-[7-(3-Fluoro-benzyloxy)-1,2,4,5-tetrahydro-benzo[d]azepin-3-yl]-3-oxo-propionic acid ethyl ester: The title compound was prepared in analogy to Example 1d) from 7-(3-fluoro-benzyloxy)-2,3,4,5-tetrahydro-1H-benzo[d]azepine hydrochloride [Example 1c)] and ethyl malonic acid chloride with triethylamine as the base. Yield: 70% of theory as a colourless oil; MS: m/e=386 (M+H)$^+$.

b) 3-[7-(3-Fluoro-benzyloxy)-1,2,4,5-tetrahydro-benzo[d]azepin-3-yl]-3-oxo-propionamide: In a sealed tube, a mixture of 23 mg (0.06 mmol) of 3-[7-(3-fluoro-benzyloxy)-1,2,4,5-tetrahydro-benzo[d]azepin-3-yl]-3-oxo-propionic acid ethyl ester and 0.7 ml (4.6 mmol) of an aqueous ammonium hydroxide solution (25%) in 0.3 ml dioxane was heated at 100° C. during 4 h. For the working-up, the reaction mixture was evaporated under reduced pressure. The residue was purified by preparative HPLC using a gradient of a 95:5-mixture to a 5:95-mixture of water and acetonitril (+0.1% of formic acid) as the eluent, and 11 mg (52% of theory) of 3-[7-(3-fluoro-benzyloxy)-1,2,4,5-tetrahydro-benzo[d]azepin-3-yl]-3-oxo-propionamide were obtained as a white solid; MS: m/e=357 (M+H)$^+$.

EXAMPLE 5

7-(3-Fluoro-benzyloxy)-1,2,4,5-tetrahydro-benzo[d]azepine-3-carboxylic Acid Methyl Ester The title compound was prepared in analogy to Example 1d) from 7-(3-fluoro-benzyloxy)-2,3,4,5-tetrahydro-1H-benzo[d]azepine hydrochloride [Example 1c)] and methyl chloroformate with triethylamine as the base. Yield: 95% of theory as a colourless oil; MS: m/e=330 (M+H)$^+$.

EXAMPLE 6

7-(3-Fluoro-benzyloxy)-1,2,4,5-tetrahydro-benzo[d]azepine-3-carbaldehyde

A mixture of 147 μl of acetic anhydride and 74 μl of formic acid was stirred at 60° C. for 2 h. Thereafter, the solution was cooled to RT, diluted with 1 ml of tetrahydrofurane, and treated with a solution of 250 mg (0.9 mmol) of 7-(3-fluoro-benzyloxy)-2,3,4,5-tetrahydro-1H-benzo[d] azepine in a mixture of 1 ml of tetrahydrofurane and 2 ml dichloromethane. Immediately after the addition, a suspension had formed which was stirred at RT during 1 h. For the working-up, the reaction mixture was diluted with dichloromethane and washed twice with water. The organic layer was separated, dried over sodium sulfate and evaporated. For purification, the material obtained (256 mg of a yellowish oil) was chromatographed on silica gel using a 99:1-mixture of dichloromethane and methanol as the eluent. There were obtained 226 mg (82% of theory) of 7-(3-fluoro-benzyloxy)-1,2,4,5-tetrahydro-benzo[d]azepine-3-carbaldehyde as a colourless oil; MS: m/e=300 (M+H)$^+$.

EXAMPLE 7

7-(3-Fluoro-benzyloxy)-3-methanesulfonyl-2,3,4,5-tetrahydro-1H-benzo[d]azepine

A solution of 200 mg (0.65 mmol) of 7-(3-fluoro-benzyloxy)-2,3,4,5-tetrahydro-1H-benzo[d]azepine hydrochloride [Example 1c] in 8 ml of tetrahydrofurane was treated with 198 μl (1.4 mmol) of triethylamine. The mixture was cooled to 0° C. and 56 μl (0.7 mmol) of methanesulfochloride were added. After 30 min at 0° C., the reaction mixture was extracted twice with water. The organic layer was separated, dried over sodium sulfate and evaporated to yield 215 mg (95% of theory) of pure 7-(3-fluoro-benzyloxy)-3-methanesulfonyl-2,3,4,5-tetrahydro-1H-benzo[d]azepine as a white solid; MS: m/e=349 (M)$^+$.

EXAMPLE 8

7-(3-Fluoro-benzyloxy)-1,2,4,5-tetrahydro-benzo[d] azepine-3-carboxylic Acid Amide A mixture of 250 mg (0.8 mmol) of 7-(3-fluoro-benzyloxy)-2,3,4,5-tetrahydro-1H-benzo[d]azepine hydrochloride [Example 1c] and 423 μl (2.4 mmol) of N-ethyl-diisopropylamine in 2 ml of N,N-dimethylformamide was treated at 0° C. with 336 μl (2.4 mmol) of trimethylsilylisocyanate. The mixture was stirred at RT for 4 h. For the working-up, the solvent was evaporated under reduced pressure, and, thereupon, the red residue dissolved in dichloromethane. The organic layer was washed twice with water, dried over sodium sulfate and evaporated. For purification, the crude material obtained (289 mg of a red solid) was chromatographed on silica gel using a 98:2-mixture of dichloromethane and methanol as the eluent. There were obtained 175 mg (68% of theory) of 7-(3-fluoro-benzyloxy)-1,2,4,5-tetrahydro-benzo[d]azepine-3-carboxylic acid amide as a white solid; MS: m/le 315 (M+H)$^+$.

EXAMPLE 9

7-(3-Fluoro-benzyloxy)-1,2,4,5-tetrahydro-benzo[d] azepine-3-carboxylic Acid Ethylamide A mixture of 50 mg (0.16 mmol) of 7-(3-fluoro-benzyloxy)-2,3,4,5-tetrahydro-1H-benzo[d]azepine hydrochloride [Example 1c] and 27 μl (0.2 mmol) of triethylamine in 1 ml of dichloromethane was treated at −20° C. with 13 μl (0.16 mmol) of ethylisocyanate. The mixture was left to warm to RT and stirred for 18 h. For the working-up, the solvent was evaporated. For purification, the crude material obtained (88 mg of a white solid) was chromatographed on silica gel using a 98:2:0.1-mixture of dichloromethane, methanol and ammonium hydroxide as the eluent. There were obtained 47 mg (85% of theory) of 7-(3-fluoro-benzyloxy)-1,2,4,5-tetrahydro-benzo[d]azepine-3-carboxylic acid ethylamide as a white solid; MS: m/e=343 (M+H)$^+$.

EXAMPLE 10

2-[7-(3-Fluoro-benzyloxy)-1,2,4,5-tetrahydro-benzo [d]azepin-3-yl]-acetamide

A solution of 70 mg (0.23 mmol) of 7-(3-fluoro-benzyloxy)-2,3,4,5-tetrahydro-1H-benzo[d]azepine hydrochloride [Example 1c] in 1 ml of acetone was successively treated with 69 mg (0.5 mmol) of potassium carbonate and 24 mg (0.25 mmol) of 2-chloroacetamide. The reaction mixture was heated to reflux during 18 h. For the working-up, 1 g of silica gel was added to the cooled reaction mixture, which was then evaporated under reduced pressure. For purification, the crude material obtained was chromatographed on silica gel using a 95:5:0.1-mixture of dichloromethane, methanol and ammonium hydroxide as the eluent. There were obtained 38 mg (51% of theory) of 2-[7-(3-fluoro-benzyloxy)-1,2,4,5-tetrahydro-benzo[d]azepin-3-yl]-acetamide as a white solid; MS: m/e 329 (M+H)$^+$.

EXAMPLE 11

(RS)-2-[7-(3-Fluoro-benzyloxy)-1,2,4,5-tetrahydro-benzo[d]azepin-3-yl]-propionamide The title compound was prepared in analogy to Example 10 from 7-(3-fluoro-benzyloxy)-2,3,4,5-tetrahydro-1H-benzo[d]azepine hydrochloride [Example 1c] and (RS)-2-bromo-propionamide with potassium carbonate as the base. Yield: 85% of theory as a white solid; MS: m/e=343 (M+H)$^+$.

EXAMPLE 12

8-(3-Fluoro-benzyloxy)-1,3-dihydro-benzo[d] azepin-2-one

In analogy to the procedure described in J. Med. Chem. 33:1496–1504 (1990), the intermediate 8-hydroxy-1,3-dihydro-benzo[d]azepin-2-one (b) was prepared in the following way:

a) 2-(3-Benzyloxy-phenyl)-N-(2,2-dimethoxy-ethyl)-acetamide: To a suspension of 5.0 g (20.6 mmol) of 3-(benzyloxy)phenylacetic acid [Synthesis 9:1214–1216 (2000)] in 50 ml of dichloromethane, 4.5 ml (62 mmol) of thionylchloride were added dropwise at RT within 10 min. The resulting yellowish solution was stirred under reflux during 90 min. After cooling, the reaction mixture was evaporated under reduced pressure and the crude acid chloride kept under HV at RT for 1 h to yield 5.38 g of a yellow-brownish oil. Thereafter, a solution of the aforementioned acid chloride in 15 ml dichloromethane was added dropwise under cooling to a solution of 2.17 g (20.6 mmol) of aminoacetaldehyde dimethylacetal and 2.09 g (20.6 mmol) of triethylamine in 30 ml of dichloromethane in a way so that the temperature was kept between 5–10° C. The reaction mixture was left to warm to RT and stirring was continued for 1 h. For the working-up, the reaction mixture was diluted with 100 ml of dichloromethane, then washed with 50 ml of water. The organic layer was separated, dried over sodium sulfate and evaporated. The obtained 6.7 g (98% of theory)

of 2-(3-benzyloxy-phenyl)-N-(2,2-dimethoxy-ethyl)-acetamide were pure enough to be engaged in the next step without further purification.

b) 8-Hydroxy-1,3-dihydro-benzo[d]azepin-2-one: A suspension of 1.0 g (3.0 mmol) of 2-(3-benzyloxy-phenyl)-N-(2,2-dimethoxy-ethyl)-acetamide in 6 ml of concentrated hydrochloric acid was treated with 6 ml of glacial acetic acid. The reaction mixture was stirred at RT during 60 h. For the working-up, the reaction mixture was hydrolysed on a mixture of ice and water. The precipitated product was collected on a filter funnel, thereafter dried under HV at RT. There were obtained 316 mg (59% of theory) of 8-hydroxy-1,3-dihydro-benzo[d]azepin-2-one as a beige powder; MS: m/e=174 (M–H)$^+$.

c) 8-(3-Fluoro-benzyloxy)-1,3-dihydro-benzo[d]azepin-2-one: A solution of 400 mg (2.3 mmol) of 8-hydroxy-1,3-dihydro-benzo[d]azepin-2-one in a mixture of 15 ml of acetone and 1 ml of N,N-dimethylformamide was treated with 351 mg (2.5 mmol) of potassium carbonate. Thereafter, 500 mg (2.5 mmol) of 3-fluorobenzylbromide were added to the orange coloured solution. The reaction mixture was stirred at 60° C. for 18 h while a brownish suspension was formed. For the working-up, the cooled reaction mixture was evaporated under reduced pressure, and the residue obtained was directly subjected to a column chromatography on silica gel using a 1:1-mixture of heptane and ethylacetate as the eluent. There were obtained 404 mg (62% of theory) of 8-(3-fluoro-benzyloxy)-1,3-dihydro-benzo[d]azepin-2-one as a yellowish powder; MS: m/e=284 (M+H)$^+$.

EXAMPLE 13

8-(3-Fluoro-benzyloxy)-3-methyl-1,3-dihydro-benzo[d]azepin-2-one

In a dried flask under an inert atmosphere, 70 mg (0.25 mmol) of 8-(3-fluoro-benzyloxy)-1,3-dihydro-benzo[d]azepin-2-one were dissolved in 5 ml of tetrahydrofurane, and the solution cooled to 0° C. Thereupon, 14 mg (0.3 mmol) of sodium hydride (50% in oil) were added and stirring continued at 0° C. for 15 min. Finally, 17 µl (0.3 mmol) of methyliodide were added. The reaction mixture was left to warm to RT and stirring continued for 90 min. For completion of the reaction, the mixture was heated to 40° C. during 2 h. For the working-up, the reaction mixture was evaporated under reduced pressure. The residue was dissolved in 10 ml of ethylacetate, the solution extracted with 4 ml of water, then dried over sodium sulfate and evaporated under reduced pressure. For purification, the crude material obtained was chromatographed on silica gel using a 2:1-mixture of heptane and ethylacetate as the eluent. There were obtained 51 mg (69% of theory) of 8-(3-fluoro-benzyloxy)-3-methyl-1,3-dihydro-benzo[d]azepin-2-one as a yellowish solid; MS: m/e=297 (M)$^+$.

EXAMPLE 14

8-(3-Fluoro-benzyloxy)-3-methoxyacetyl-1,3-dihydro-benzo[d]azepin-2-one

In a dried flask under an inert atmosphere, 50 mg (0.18 mmol) of 8-(3-fluoro-benzyloxy)-1,3-dihydro-benzo[d]azepin-2-one were dissolved in 3 ml of dichloromethane, and the solution cooled to 0° C. Thereupon, 21 mg (0.21 mmol) triethylamine were added and stirring continued at 0° C. Finally, 18 µl (0.2 mmol) of methoxyacetic acid chloride were added. The reaction mixture was left to warm to RT and stirring continued for 18 h. For the working-up, the reaction mixture was evaporated under reduced pressure. For purification, the crude material obtained was directly transferred on a column and chromatographed on silica gel using a 99:1-mixture of dichloromethane and methanol as the eluent. There were obtained 15 mg (24% of theory) of 8-(3-fluoro-benzyloxy)-3-methoxyacetyl-1,3-dihydro-benzo[d]azepin-2-one as a white powder; MS: m/e=356 (M+H)$^+$.

EXAMPLE 15

3-Acetyl-8-(3-fluoro-benzyloxy)-1,3-dihydro-benzo[d]azepin-2-one

In a dried flask under an inert atmosphere, 103 mg (0.36 mmol) of 8-(3-fluoro-benzyloxy)-1,3-dihydro-benzo[d]azepin-2-one and 72 mg (0.9 mmol) of sodium acetate were suspended in 0.3 ml of acetic acid anhydride. The solution was heated to 140° C. for 4 h. For the working-up, the reaction mixture was cooled, then evaporated under reduced pressure. The residue was treated with 1.5 ml of ice/water and 4 ml of ethyl acetate. The aqueous layer was separated and re-extracted with 4 ml of ethyl acetate. The combined organic layers were dried over sodium sulfate, thereafter the solvent evaporated under reduced pressure. For purification, the crude material obtained was chromatographed on silica gel using a gradient of heptane to a 4:1-mixture of heptane and ethyl acetate as the eluent. There were obtained 91 mg (77% of theory) of 3-acetyl-8-(3-fluoro-benzyloxy)-1,3-dihydro-benzo[d]azepin-2-one as a light yellow solid; MS: m/e=325 (M)$^+$.

EXAMPLE 16

8-(3-Fluoro-benzyloxy)-1,3,4,5-tetrahydro-benzo[d]azepin-2-one a) 8-Hydroxy-1,3,4,5-tetrahydro-benzo[d]azepin-2-one: 70 mg (0.4 mmol) of 8-(3-fluoro-benzyloxy)-1,3-dihydro-benzo[d]azepin-2-one were dissolved in 2 ml of ethanol. After addition of 22 mg of palladium (10% on charcoal), hydrogenation was performed at RT and atmospheric pressure. After 60 h, the catalyst was filtered off and the solvent evaporated to yield 62 mg (88% of theory) of crude 8-hydroxy-1,3,4,5-tetrahydro-benzo[d]azepin-2-one which was engaged in the next step without further purification; MS: m/e=176 (M–H)$^+$.

b) 8-(3-Fluoro-benzyloxy)-1,3,4,5-tetrahydro-benzo[d]azepin-2-one: A solution of 719 mg (4.1 mmol) of 8-hydroxy-1,3,4,5-tetrahydro-benzo[d]azepin-2-one in 30 ml of acetone was treated with 664 mg (4.8 mmol) of potassium carbonate. Thereafter, 883 mg (4.7 mmol) of 3-fluorobenzylbromide were added to the solution and the reaction mixture was stirred at 50° C. for 36 h. For the working-up, the cooled reaction mixture was evaporated under reduced pressure, and the residue obtained was directly subjected to a column chromatography on silica gel using a 99:1-mixture of dichloromethane and methanol as the eluent. There were obtained 210 mg (18% of theory) of 8-(3-fluoro-benzyloxy)-1,3,4,5-tetrahydro-benzo[d]azepin-2-one as a yellowish powder; MS: m/e=286 (M+H)$^+$.

EXAMPLE 17

7-(2,3,4-Trifluoro-benzyloxy)-1,3,4,5-tetrahydro-benzo[d]azepin-2-one and 7-(2,3,4-trifluoro-benzyloxy)-1,2,4,5-tetrahydro-benzo[c]azepin-3-one a) 7-Methoxy-1,3,4,5-tetrahydro-benzo[d]azepin-2-one and 7-methoxy-1,2,4,5-tetrahydro-benzo[d]azepin-3-one: A mixture of 500 mg (2.7 mmol) of 6-methoxy-tetralone and 350 mg (5.4 mmol) of sodium azide in 3.4 ml of acetic acid was heated to 70° C. Thereafter, 0.85 ml (15.2 mmol) of sulfuric acid was added dropwise in a manner so that a temperature of 70° C. was maintained. After complete addition, the reaction mixture was hydrolysed on ice, then neutralized with solid sodium hydrogencarbonate, and extracted with dichloromethane. The organic layer was separated, dried over sodium sulfate and evaporated. For purification, the residue was chromatographed on silica gel using a 95:5-mixture of dichloromethane and methanol as the eluent. There were obtained 200 mg (39% of theory) of the mixture of 7-methoxy-1,3,4,5-tetrahydro-benzo[d]azepin-2-one and 7-methoxy-1,2,4,5-tetrahydro-benzo[d]azepin-3-one as a brown solid; MS: m/e=192 (M+H)$^+$.

b) 7-Hydroxy-1,3,4,5-tetrahydro-benzo[d]azepin-2-one and 7-hydroxy-1,2,4,5-tetrahydro-benzo[c]azepin-3-one: A solution of 200 mg (1.0 mmol) of a mixture of 7-methoxy-1,3,4,5-tetrahydro-benzo[d]azepin-2-one and 7-methoxy-1,2,4,5-tetrahydro-benzo[d]azepin-3-one in 4 ml dichloromethane was cooled to 0° C. and treated dropwise with 4.18 ml (4.2 mmol) of bromotribromide. The reaction mixture was left to warm to RT and stirring was continued for 1 hour. For the working-up, the mixture was treated with 1.05 ml (2.1 mmol) of a solution of sodium hydroxide (2 M) and extracted with dichloromethane. The aqueous layer was acidified and extracted with ethyl acetate. The organic layer was dried over sodium sulfate and, thereafter, evaporated under reduced pressure. The crude mixture of isomers, 74 mg of a brown solid, was engaged in the next step without further purification and characterisation; MS: m/e=178 (M+H)$^+$.

c) 7-(2,3,4-Trifluoro-benzyloxy)-1,3,4,5-tetrahydrobenzo[d]azepin-2-one and 7-(2,3,4-trifluoro-benzyloxy)-1,2,4,5-tetrahydro-benzo[c]azepin-3-one: A mixture of 60 mg (0.34 mmol) of 7-hydroxy-1,3,4,5-tetrahydro-benzo[d]azepin-2-one and 7-hydroxy-1,2,4,5-tetrahydro-benzo[c]azepin-3-one, 94 mg (0.7 mmol) of potassium carbonate and 86 mg (0.37 mmol) of 2,3,4-trifluorobenzylbromide in 4 ml of 2 butanone was heated at 90° C. during 18 hours. For the working-up, the reaction mixture was cooled and evaporated under reduced pressure. For purification, the crude product was chromatographed on silical gel using a 98:2-mixture of dichloromethane and methanol as the eluent. There were obtained 50 mg (46% of theory) of a 3:4-mixture of 7-(2,3,4-trifluoro-benzyloxy)-1,3,4,5-tetrahydro-benzo[d]azepin-2-one and 7-(2,3,4-trifluoro-benzyloxy)-1,2,4,5-tetrahydro-benzo[c]azepin-3-one as a light yellow solid; MS: m/e=322 (M+H)$^+$.

EXAMPLE 18

7-(2,6-Difluoro-benzyloxy)-1,3,4,5-tetrahydro-benzo[d]azepin-2-one and 7-(2,6-difluoro-benzyloxy)-1,2,4,5-tetrahydro-benzo[c]azepin-3-one In an analogous manner to that described in Example 17 c), the alkylation of the mixture of 7-hydroxy-1,3,4,5-tetrahydro-benzo[d]azepin-2-one and 7-hydroxy-1,2,4,5-tetrahydro-benzo[c]azepin-3-one [Example 17 b)] by 2,6-difluorobenzylbromide in the presence of potassium carbonate in 2-butanone yielded the mixture of 7-(2,6-difluoro-benzyloxy)-1,3,4,5-tetrahydro-benzo[d]azepin-2-one and 7-(2,6-difluoro-benzyloxy)-1,2,4,5-tetrahydro-benzo[c]azepin-3-one.

The aforementioned mixture of isomers was separated on a preparative HPLC column using a 4:1 mixture of n-heptane and ethanol as the eluent. There were obtained in a 2:7-ratio the first eluting 7-(2,6-difluoro-benzyloxy)-1,2,4,5-tetrahydro-benzo[c]azepin-3-one [MS: m/e=304 (M+H)$^+$] and the later eluting isomer 7-(2,6-difluoro-benzyloxy)-1,3,4,5-tetrahydro-benzo[d]azepin-2-one [MS: m/e=304 (M+H)$^+$], each as a white solid.

EXAMPLE 19

7-Benzyloxy-1,3,4,5-tetrahydro-benzo[d]azepin-2-one a) 7-Methoxy-1,3,4,5-tetrahydro-benzo[d]azepin-2-one and 7-methoxy-1,2,4,5-tetrahydro-benzo[c]azepin-3-one: A mixture of 500 mg (2.8 mmo) of 6-methoxy-2-tetralone and 354 mg (5.4 mmol) of sodium azide in 3.4 ml of acetic acid was heated to 70° C. Then, 0.85 ml of sulfuric acid (96%) were added dropwise in such a manner that the temperature was kept at 70° C. After the complete addition, stirring was continued for 15 min. For the working-up, the reaction mixture was hydrolysed on ice, thereupon neutralized by addition of sodium hydroxide-solution (2M) and extracted with dichloromethane. For purification, the crude material obtained was chromatographed on silica gel using a 99:1-mixture of dichloromethane and methanol as the eluent. Of the first eluting isomer, 7-methoxy-1,3,4,5-tetrahydro-benzo[d]azepin-2-one, there were obtained 180 mg (35% of theory) as a light brown solid [MS: m/e=191 (M)$^+$], and of the second isomer, 7-methoxy-1,2,4,5-tetrahydro-benzo[c]azepin-2-one, there were obtained 73 mg (14% of theory) as a light brown solid [MS: m/e=191 (M)$^+$].

b) 7-Hydroxy-1,3,4,5-tetrahydro-benzo[d]azepin-2-one: A solution of 1.07 g (5.6 mmol) of 7-methoxy-1,3,4,5-tetrahydro-benzo[d]azepin-2-one in 10 ml of dichloromethane was treated at 0° C. with 22.3 ml of a solution of borontribromide in dichloromethane (1M). After stirring for 1 h at RT, the reaction mixture was evaporated, and the residue was directly submitted to chromatography using a 95:5-mixture of dichloromethane and methanol as the eluent. There were obtained 625 mg (63% of theory) of 7-hydroxy-1,3,4,5-tetrahydro-benzo[d]azepin-2-one as a light brown solid; MS: m/e 178 (M+H)$^+$.

c) 7-Benzyloxy-1,3,4,5-tetrahydro-benzo[d]azepin-2-one: In an analogous manner to that described in Example 17 c), the alkylation of 7-hydroxy-1,3,4,5-tetrahydro-benzo[d]azepin-2-one by benzylbromide in presence of potassium carbonate in 2-butanone at 90° C. yielded the 7-benzyloxy-1,3,4,5-tetrahydro-benzo[d]azepin-2-one as a white solid; MS: m/e=268 (M+H)$^+$.

EXAMPLE 20

7-(3-Fluoro-benzyloxy)-1,3,4,5-tetrahydro-benzo[d]azepin-2-one

In an analogous manner to that described in Example 17 c), the alkylation of 7-hydroxy-1,3,4,5-tetrahydro-benzo[d]azepin-2-one [Example 19 b)] by 3-fluorobenzylbromide in the presence of potassium carbonate in 2-butanone yielded the 7-(3-fluoro-benzyloxy)-1,3,4,5-tetrahydro-benzo[d]azepin-2-one as a white solid; MS: m/e=286 (M+H)$^+$.

EXAMPLE 21

7-(3-Chloro-benzyloxy)-1,3,4,5-tetrahydro-benzo[d]azepin-2-one

In an analogous manner to that described in Example 17 c), the alkylation of 7-hydroxy-1,3,4,5-tetrahydro-benzo[d]azepin-2-one [Example 19 b)] by 3-chlorobenzylbromide in the presence of potassium carbonate in 2-butanone yielded the 7-(3-chloro-benzyloxy)-1,3,4,5-tetrahydro-benzo[d] azepin-2-one as a white solid; MS: m/e=302 (M+H)$^+$.

EXAMPLE 22

3-Acetyl-7-(3-chloro-benzyloxy)-1,3,4,5-tetrahydro-benzo[d]azepin-2-one

A mixture of 50 mg (0.2 mmol) of 7-(3-chloro-benzyloxy)-1,3,4,5-tetrahydro-benzo[d]azepin-2-one and 33 mg (0.4 mmol) of sodium acetate in 0.12 ml of acetic acid anhydride was heated to 145° C. during 4.5 hours. For the working-up, the reaction mixture was cooled and treated with water and dichloromethane. The organic layer was separated, washed with a saturated solution of sodium hydrogencarbonate, and, finally, evaporated. For purification, the crude material obtained was chromatographed on silica gel using a 4:1-mixturet of heptane and ethyl acetate as the eluent. There were obtained 45 mg (79% of theory) of 3-acetyl-7-(3-chloro-benzyloxy)-1,3,4,5-tetrahydro-benzo[d]azepin-2-one as a white foam; MS: m/e=344 (M+H)$^+$.

EXAMPLE 23

7-(3-Fluoro-benzyloxy)-1,2,4,5-tetrahydro-benzo[c]azepin-2-one a) 7-Hydroxy-1,2,4,5-tetrahydro-benzo[c]azepin-2-one: In an analogous manner to that described in Example 19 b), the ether cleavage of the 7-methoxy-1,2,4,5-tetrahydro-benzo[c]azepin-2-one [Example 19 a)] by boron tribromide yielded the 7-hydroxy-1,2,4,5-tetrahydro-benzo[c]azepin-2-one as a white solid; MS: m/e=178 (M+H)$^+$.

b) 7-(3-Fluoro-benzyloxy)-1,2,4,5-tetrahydro-benzo[c]azepin-2-one: In an analogous manner to that described in Example 17 c), the alkylation of the 7-hydroxy-1,2,4,5-tetrahydro-benzo[c]azepin-2-one by 3-fluoro-benzylbromide in the presence of potassium carbonate in 2-butanone yielded the 7-(3-fluoro-benzyloxy)-1,2,4,5-tetrahydro-benzo[c]azepin-2-one as a white solid; MS: m/e=286 (M+H)$^+$.

Compounds of formula I and their pharmaceutically acceptable salts, as individual isomers of the compounds of formula I as well as racemic and non-racemic mixtures thereof (hereinafter: Pharmaceutical Compound) have pharmacological activity and are useful as pharmaceuticals. In particular, Pharmaceutical Compounds selectively inhibit the activity of monoamine oxidase B.

The pharmacological activity of the Pharmaceutical Compounds can be demonstrated, e.g. as follows:

The cDNA's encoding human MAO-A and MAO-B were transiently transfected into EBNA cells using the procedure described by Schlaeger and Christensen [Cytotechnology 15:1–13 (1998)]. After transfection, cells were homogenised by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing step with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by Zhou and Panchuk-Voloshina [Analytical Biochemistry 253:169–174 (1997)]. Briefly, membrane aliquots were incubated in 0.1 M potassium phosphate buffer, pH 7.4, for 30 min at 37° C. with or without various concentrations of the compounds. After this period, the enzymatic reaction was started by the addition of the MAO substrate tyramine together with 1 U/ml horseradish peroxidase (Roche Biochemicals) and 80 μM N-acetyl-3,7,-dihydroxyphenoxazine (Amplex Red, Molecular Probes). The samples were further incubated for 30 min at 37° C. in a final volume of 200 μl and absorbance was then determined at a wavelength of 570 nm using a SpectraMax plate reader (Molecular Devices). Background (non-specific) absorbance was determined in the presence of 10 μM clorgyline for MAO-A or 10 μM L-deprenyl for MAO-B.

$IC_{50}$ values were determined from inhibition curves obtained using nine inhibitor concentrations in duplicate, by fitting data to a four parameter logistic equation using a computer program.

The compounds of the present invention are specific MAO-B inhibitors. The $IC_{50}$ values of compounds of formula I as measured in the assay described above are in the range of 10 μM or less, typically of 1 μM or less, and ideally 0.1 μM or less. The below table shows exemplary $IC_{50}$ values:

| Example | human MAO-B [$IC_{50}$ (μM)] | human MAO-A [$IC_{50}$ (μM)] |
| --- | --- | --- |
| 1 | 0.082 | >10 |
| 2 | 0.073 | 5.5 |
| 3 | 0.024 | >10 |
| 5 | 0.068 | 4.5 |
| 6 | 0.007 | 4.1 |
| 8 | 0.021 | >10 |
| 13 | 0.15 | 4.6 |
| 15 | 0.13 | >9.5 |

In another aspect, the present invention provides medicaments, i.e. pharmaceutical compositions, based on a compound in accordance with the invention and their manufacture as well as the use of the compounds in the control or prevention of diseases mediated by monoamine oxidase B inhibitors, and, respectively, for the production of corresponding medicaments.

Pharmaceutical Compounds can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The present invention provides pharamceutical compositions containing Pharmaceutical Compounds and a pharmaceutically acceptable carrier. Such compositions can be in the form of tablets, coated tablets, dragees, hard and soft gelatine capsules, solutions, emulsions or suspensions. The pharmaceutical compositions also can be in the form of suppositories or injectable solutions.

The compositions of the invention, in addition to one or more Pharmaceutical Compounds, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, e.g., as such carriers for tablets, coated tablets, dragées and hard gelatine capsules. Suitable carriers for soft gelatine capsules are, e.g., vegetable oils, waxes, fats, semi-solid and liquid polyols and the like; depending on the nature of the active substance no carriers are, however, usually required in the case of soft gelatine capsules. Suitable carriers for the production of solutions and syrups are, e.g., water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, e.g., natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain other therapeutically valuable substances.

As mentioned earlier, compositions containing Pharmaceutical Compound and a therapeutically inert carrier are also an object of the present invention, as is a process for the production of such compositions which comprises bringing one or more Pharmaceutical Compounds and, if desired, one or more other therapeutically valuable substances into a galenical dosage form together with one or more therapeutically inert carriers.

Pharmaceutical Compounds are accordingly useful as selective inhibitors of monoamine oxidase B, e.g. in the treatment or prevention of diseases and conditions in which activity of monoamine oxidase B plays a role or is implicated. Such conditions include in particular acute and/or chronic neurological disorders.

Acute and/or chronic neurological disorders include psychosis, schizophrenia, Alzheimer's disease, cognitive disorders and memory deficits like mild cognitive impairment, age-related cognitive decline, vascular dementia, Parkinsons's disease, memory impairment associated with depression or anxiety, Down's syndrome, stroke, traumatic brain injury, and attention deficit disorder. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychotic episodes, opiate addiction, anxiety, vomiting, dyskinesia and depression.

In one embodiment, the acute and/or chronic neurological disorder is Alzheimer's disease.

In another embodiment, the acute and/or chronic neurological disorder is mild cognitive impairment or senile dementia.

Thus, the present invention provides a method for treating Alzheimer's disease in a patient in need thereof which comprises administering a therapeutically effective amount of a compound of formula I. The invention also provides a method for treating mild cognitive impairment or senile dementia in a patient in need thereof which comprises administering a therapeutically effective amount of a compound of formula I.

The Pharmaceutical Compounds and compositions of the invention can be administered in a conventional manner, for example, orally, rectally, or parenterally. The pharmaceutical compositions of the invention can be administered orally, for example, in the form of tablets, coated tablets, dragees, hard and soft gelatine capsules, solutions, emulsions or suspensions. The pharmaceutical compositions also can be administered rectally, for example, in the form of suppositories or parenterally, for example, in the form of injectable solutions.

The dosage at which the compound can be administered can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

EXAMPLE A

Tablets

Tablets of the following composition are produced in a conventional manner:

|  | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets

Tablets of the following composition are produced in a conventional manner:

|  | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules

Capsules of the following composition are produced:

|  | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

Injection Solution

An injection solution can have the following composition and is manufactured in the usual manner:

| | |
|---|---|
| Active substance | 1.0 mg |
| 1 N HCl | 20.0 µl |
| acetic acid | 0.5 mg |
| NaCl | 8.0 mg |
| phenol | 10.0 mg |
| 1 N NaOH | q.s. ad pH 5 |
| H$_2$O | q.s. ad 1 ml |

In accordance with the foregoing the present invention also provides:
(a) A pharmaceutical compound for use as a selective inhibitor of monoamine oxidase B activity, for example for use in any of the particular indications as hereinbefore set forth;
(b) A pharmaceutical composition comprising a pharmaceutical compound as under (a) as active ingredient together with a pharmaceutically acceptable diluent or carrier therefor;
(c) A pharmaceutical composition for the treatment or prevention of a disease or condition in which selective inhibition of monoamine oxidase B activity plays a role or is implicated comprising a pharmaceutical compound as under (a) and a carrier;
(d) A method for the treatment of any of the particular indications hereinbefore set forth in a subject in need thereof which comprises administering a therapeutically effective amount of a pharmaceutical compound as under (a);
(e) A method for treating or preventing a disease or condition in which selective inhibition of monoamine oxidase B activity plays a role or is implicated comprising administering to a subject in need thereof a therapeutically effective amount of a pharmaceutical compound as under (a);
(f) Use of a pharmaceutical compound as under (a) for the manufacture of a medicament for the treatment or prevention of a disease or condition in which selective inhibition of monoamine oxidase B activity plays a role or is implicated;
(g) A process for the preparation of a compound as under (a).

What is claimed is:
1. A compound of formula I

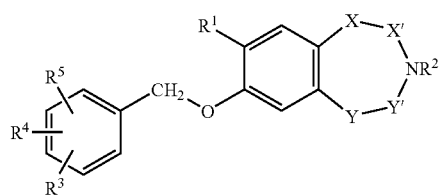

wherein
$R^1$ is hydrogen or methyl;
$R^2$ is hydrogen, $(C_1-C_3)$-alkyl, $-CH_2C(O)NH_2$, $-CH(CH_3)C(O)NH_2$, $-S(O)_2CH_3$ or $-C(O)R^6$;
$R^3$, $R^4$ and $R^5$ are each independently hydrogen, halogen, cyano, $(C_1-C_3)$-alkyl or $-O-(C_1-C_3)$-alkyl;
$R^6$ is hydrogen, $-CH_3$, $-CH_2OCH_3$, $-C(O)NH_2$, $-CH_2C(O)NH_2$, $-OCH_3$, $-NH_2$ or $-NHCH_2CH_3$,
X–X' is $-CH_2-CH_2-$ or $-CH=CH-$; and
Y–Y' is $-CH_2-CH_2-$ or $-CH=CH-$;
wherein X–X' and Y–Y' are not both $-CH_2-CH_2-$ and
wherein when one of X–X' and Y–Y' is $-CH_2-CH_2-$ and the other is $-CH=CH-$, or when both of X–X' and Y–Y' are $-CH=CH-$, then $R^2$ is $-S(O)_2CH_3$ or $-C(O)R^6$;
or a pharmaceutically acceptable salt thereof.

2. The compound of formula I according to claim 1 wherein $R^1$ is hydrogen.

3. The compound of formula I according to claim 1 wherein $R^2$ is hydrogen.

4. The compound of formula I according to claim 1 wherein $R^2$ is $-CH_3$, $-CH_2C(O)NH_2$, $-CH(CH_3)C(O)NH_2$, $-S(O)_2CH_3$ or $-C(O)R^6$ wherein $R^6$ is hydrogen, $-CH_3$, $-CH_2OCH_3$, $-C(O)NH_2$, $-CH_2C(O)NH_2$, $-OCH_3$, $-NH_2$ or $-NHCH_2CH_3$.

5. The compound of formula I according to claim 4 wherein $R^2$ is $-CH_3$, $-CH_2C(O)NH_2$ or $-CH(CH_3)C(O)NH_2$.

6. The compound of formula I according to claim 4 wherein $R^2$ is $-S(O)_2CH_3$ or $-C(O)R^6$, wherein $R^6$ is hydrogen, $-CH_3$, $-CH_2OCH_3$, $-C(O)NH_2$, $-CH_2C(O)NH_2$, $-OCH_3$, $-NH_2$ or $-NHCH_2CH_3$.

7. The compound of formula I according to claim 1 wherein $R^3$, $R^4$ and $R^5$ independently are hydrogen or halogen.

8. The compound of formula I according to claim 7 wherein $R^3$, $R^4$, and $R^5$ are hydrogen.

9. The compound of formula I according to claim 7 wherein $R^3$ and $R^4$ are hydrogen and $R^5$ is fluorine.

10. The compound of formula I according to claim 7 wherein $R^3$, $R^4$, and $R^5$ are fluorine.

11. The compound of formula I according to claim 7 wherein $R^3$ is hydrogen and $R^4$ and $R^5$ are fluorine.

12. The compound of formula I according to claim 1 wherein
$R^1$ is hydrogen;
$R^2$ is hydrogen, $-CH_3$, $-CH_2C(O)NH_2$, $-CH(CH_3)C(O)NH_2$, $-S(O)_2CH_3$ or $-C(O)R^6$;
$R^3$, $R^4$ and $R^5$ are each independently hydrogen, halogen, cyano, $(C_1-C_3)$-alkyl or $-O-(C_1-C_3)$-alkyl;
$R^6$ is hydrogen, $-CH_3$, $-CH_2OCH_3$, $-C(O)NH_2$, $-CH_2C(O)NH_2$, $-OCH_3$, $-NH_2$ or $-NHCH_2CH_3$,
X–X' is $-CH_2-CH_2-$ or $-CH=CH-$; and
Y–Y' is $-CH_2-CH_2-$ or $-CH=CH-$;
wherein X–X' and Y–Y' are not both $-CH_2-CH_2-$ and
wherein when one of X–X' and Y–Y' is $-CH_2-CH_2-$ and the other is $-CH=CH-$, or when both of X–X' and Y–Y' are $-CH=CH-$, then $R^2$ is $-S(O)_2CH_3$ or $-C(O)R^6$.

13. A process for the preparation of a compound of formula I in accordance with claim 1

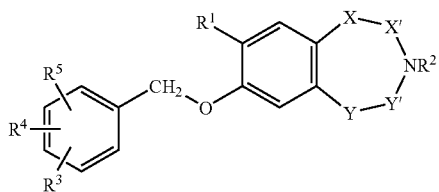

wherein
- $R^1$ is hydrogen or methyl;
- $R^2$ is hydrogen;
- $R^3$, $R^4$ and $R^5$ independently are hydrogen, halogen, cyano, $(C_1–C_3)$-alkyl or —O—$(C_1–C_3)$-alkyl;
- X–X' is —$CH_2$—$CH_2$— or —CH=CH—; and
- Y–Y' is —$CH_2$—$CH_2$— or —CH=CH—;
- wherein X–X' and Y–Y' are not both —$CH_2$—$CH_2$— and wherein when one of X–X' and Y–Y' is —$CH_2$—$CH_2$— and the other is —CH=CH—, or when both of X–X' and Y–Y' are —CH=CH—, then $R^2$ is —$S(O)_2CH_3$ or —$C(O)R^6$;

comprising cleaving a protecting group $P^1$ off a compound of formula II

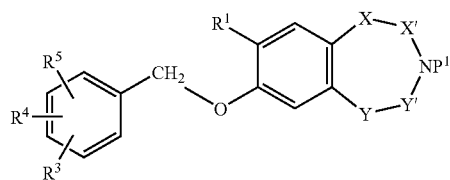

wherein $P^1$ is a protecting group selected from the group consisting of a tert-butoxycarbonyl, a methoxycarbonyl or 9-fluorenyl-methoxycarbonyl group.

14. A process for the preparation of a compound of formula I in accordance with claim 1

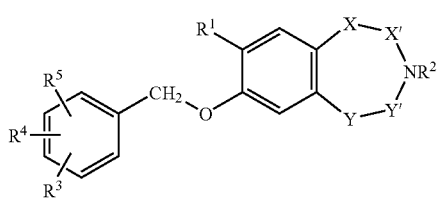

wherein
- $R^1$ is hydrogen or methyl;
- $R^2$ is hydrogen, $(C_1–C_3)$-alkyl, —$CH_2C(O)NH_2$, —CH$(CH_3)C(O)NH_2$, —$S(O)_2CH_3$ or —$C(O)R^6$;
- $R^3$, $R^4$ and $R^5$ independently are hydrogen, halogen, cyano, $(C_1–C_3)$-alkyl or —O—$(C_1–C_3)$-alkyl;
- $R^6$ is hydrogen, —$CH_3$, —$CH_2OCH_3$, —$C(O)NH_2$, —$CH_2C(O)NH_2$, —$OCH_3$, —$NH_2$ or —$NHCH_2CH_3$,
- X–X' is —$CH_2$—$CH_2$— or —CH=CH—; and
- Y–Y' is —$CH_2$—$CH_2$— or —CH=CH—;
- wherein X–X' and Y–Y' are not both —$CH_2$—$CH_2$— and wherein when one of X–X' and Y–Y' is —$CH_2$—$CH_2$— and the other is —CH=CH—, or when both of X–X' and Y–Y' are —CH=CH—, then $R^2$ is —$S(O)_2CH_3$ or —$C(O)R^6$;

comprising reacting a compound of formula III

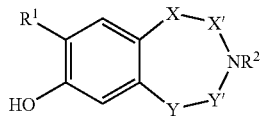

with a compound of formula IV

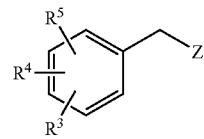

wherein Z is OH, or, when $R^2$ is —$S(O)_2CH_3$ or —$C(O)R^6$, then Z may also be halogen or a sulfonic acid residue.

15. A process for the preparation of a compound of formula I in accordance with claim 1

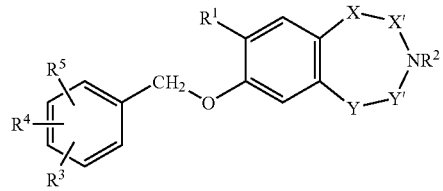

wherein
- $R^1$ is hydrogen or methyl;
- $R^2$ is —$S(O)_2CH_3$ or —$C(O)R^6$;
- $R^3$, $R^4$ and $R^5$ independently hydrogen, halogen, cyano, $(C_1–C_3)$-alkyl or —O—$(C_1–C_3)$-alkyl;
- $R^6$ is hydrogen, —$CH_3$, —$CH_2OCH_3$, —$OCH_3$, —$NH_2$ or —$NHCH_2CH_3$,
- X–X' is —$CH_2$—$CH_2$— or —CH=CH—; and
- Y–Y' is —$CH_2$—$CH_2$— or —CH=CH—;
- wherein X–X' and Y–Y' are not both —$CH_2$—$CH_2$— and
- wherein X–X' and Y–Y' are not —$CH_2$—C(O)— at the same time;

comprising reacting a compound of formula I wherein $R^2$ is hydrogen, with an activated acyl derivative; or by a condensation reaction of an acid using a condensation reagent; or by reaction with an activated sulfonyl derivative; or by reaction with an isocyanate.

16. A process for the preparation of a compound of formula I in accordance with claim 1

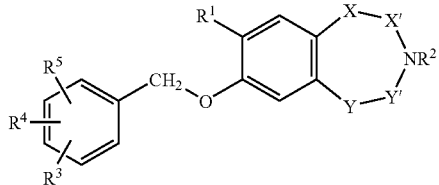

wherein
$R^1$ is hydrogen or methyl;
$R^2$ is —S(O)$_2$CH$_3$ or —C(O)R$^6$;
$R^3$, $R^4$ and $R^5$ independently hydrogen, halogen, cyano, (C$_1$–C$_3$)-alkyl or —O—(C$_1$–C$_3$)-alkyl;
$R^6$ is —C(O)NH$_2$ or —CH$_2$C(O)NH$_2$,
X–X' is —CH$_2$—CH$_2$— or —CH═CH—; and
Y–Y' is —CH$_2$—CH$_2$— or —CH═CH—;
wherein X–X' and Y–Y' are not —CH$_2$—CH$_2$— at the same time;
comprising reacting a compound of formula I wherein $R^2$ is hydrogen, with an activated acyl derivative; or by a condensation reaction of an acid using a condensation reagent; and converting the resulting ester function into a corresponding amide.

17. A pharmaceutical composition comprising a compound of formula I

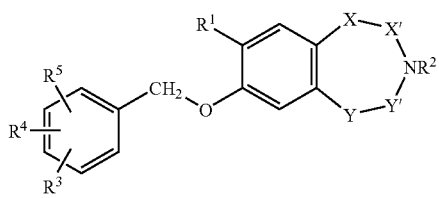

wherein
$R^1$ is hydrogen or methyl;
$R^2$ is hydrogen, (C$_1$–C$_3$)-alkyl, —CH$_2$C(O)NH$_2$, —CH(CH$_3$)C(O)NH$_2$, —S(O)$_2$CH$_3$ or —C(O)R$^6$;
$R^3$, $R^4$ and $R^5$ are each independently hydrogen, halogen, cyano, (C$_1$–C$_3$)-alkyl or —O—(C$_1$–C$_3$)-alkyl;
$R^6$ is hydrogen, —CH$_3$, —CH$_2$OCH$_3$, —C(O)NH$_2$, —CH$_2$C(O)NH$_2$, —OCH$_3$, —NH$_2$ or —NHCH$_2$CH$_3$,
X–X' is —CH$_2$—CH$_2$— or —CH═CH—; and
Y–Y' is —CH$_2$—CH$_2$— or —CH═CH—;
wherein X–X' and Y–Y' are not both —CH$_2$—CH$_2$— and
wherein when one of X–X' and Y–Y' is —CH$_2$—CH$_2$— and the other is —CH═CH—, or when both of X–X' and Y–Y' are —CH═CH—, then $R^2$ is —S(O)$_2$CH$_3$ or —C(O)R$^6$;
or a pharmaceutically acceptable salt thereof
and a pharmaceutically acceptable diluent or carrier therefor.

18. A compound of formula I

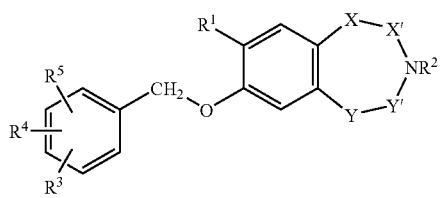

wherein
$R^1$ is hydrogen or methyl;
$R^2$ is —CH$_2$C(O)NH$_2$, —CH(CH$_3$)C(O)NH$_2$, —S(O)$_2$CH$_3$ or —C(O)R$^6$;
$R^3$, $R^4$ and $R^5$ are each independently hydrogen, halogen, cyano, (C$_1$–C$_3$)-alkyl or —O—(C$_1$–C$_3$)-alkyl;
$R^6$ is hydrogen, —CH$_3$, —CH$_2$OCH$_3$, —C(O)NH$_2$, —CH$_2$C(O)NH$_2$, —OCH$_3$, —NH$_2$ or —NHCH$_2$CH$_3$,
X–X' is —CH$_2$—CH$_2$— or —CH═CH— and
Y–Y' is —CH$_2$—CH$_2$— or —CH═CH—
wherein when one of X–X' and Y–Y' is —CH$_2$—CH$_2$— and the other is —CH═CH—, or when both of X–X' and Y–Y' are —CH═CH—, then $R^2$ is —S(O)$_2$CH$_3$ or —C(O)R$^6$
or a pharmaceutically acceptable salt thereof.

19. The compound of formula I according to claim 18 wherein $R^1$ is hydrogen.

20. The compound of formula I according to claim 18 wherein $R^2$ is —CH$_2$C(O)NH$_2$, —CH(CH$_3$)C(O)NH$_2$, —S(O)$_2$CH$_3$ or —C(O)R$^6$ wherein $R^6$ is hydrogen, —CH$_3$, —CH$_2$OCH$_3$, —C(O)NH$_2$, —CH$_2$C(O)NH$_2$, —OCH$_3$, —NH$_2$ or —NHCH$_2$CH$_3$.

21. The compound of formula I according to claim 20 wherein $R^2$ is —CH$_3$, —CH$_2$C(O)NH$_2$ or —CH(CH$_3$)C(O)NH$_2$.

22. The compound of formula I according to claim 20 wherein $R^2$ is —S(O)$_2$CH$_3$ or —C(O)R$^6$, wherein $R^6$ is hydrogen, —CH$_3$, —CH$_2$OCH$_3$, —C(O)NH$_2$, —CH$_2$C(O)NH$_2$, —OCH$_3$, —NH$_2$ or —NHCH$_2$CH$_3$.

23. The compound of formula I according to claim 18 wherein $R^3$, $R^4$ and $R^5$ independently are hydrogen or halogen.

24. The compound of formula I according to claim 23 wherein $R^3$, $R^4$, and $R^5$ are hydrogen.

25. The compound of formula I according to claim 23 wherein $R^3$ and $R^4$ are hydrogen and $R^5$ is fluorine.

26. The compound of formula I according to claim 23 wherein $R^3$, $R^4$, and $R^5$ are fluorine.

27. The compound of formula I according to claim 23 wherein $R^3$ is hydrogen and $R^4$ and $R^5$ are fluorine.

28. The compound of formula I according to claim 18 wherein X–X' is —CH$_2$—CH$_2$— and Y–Y' is —CH$_2$—CH$_2$—.

29. The compound of formula I according to claim 18 wherein
$R^1$ is hydrogen;
$R^2$ is —CH$_2$C(O)NH$_2$, —CH(CH$_3$)C(O)NH$_2$, —S(O)$_2$CH$_3$ or —C(O)R$^6$;
$R^3$, $R^4$ and $R^5$ are each independently hydrogen, halogen, cyano, (C$_1$–C$_3$)-alkyl or —O—(C$_1$–C$_3$)-alkyl;
$R^6$ is hydrogen, —CH$_3$, —CH$_2$OCH$_3$, —C(O)NH$_2$, —CH$_2$C(O)NH$_2$, —OCH$_3$, —NH$_2$ or —NHCH$_2$CH$_3$,
X–X' is —CH$_2$—CH$_2$— or —CH═CH—; and
Y–Y' is —CH$_2$—CH$_2$— or —CH═CH—; or X–X' is —CH$_2$— and Y–Y' is —CH$_2$—CH$_2$—C(O)—;
wherein when one of X–X' and Y–Y' is —CH$_2$—CH$_2$— and the other is —CH=CH—, or when both of X–X' and Y–Y' are —CH=CH—, then R$^2$ is —S(O)$_2$CH$_3$ or —C(O)R$^6$.

30. The compound of claim 29 wherein X–X' and Y–Y' are —CH$_2$—CH$_2$—.

31. The compound of formula I according to claim 18 wherein
R$^1$ is hydrogen;
R$^2$ is —CH$_2$C(O)NH$_2$, —CH(CH$_3$)C(O)NH$_2$, —S(O)$_2$CH$_3$ or —C(O)R$^6$;
R$^3$ is halogen;
R$^4$ and R$^5$ are each independently hydrogen or halogen;
R$^6$ is hydrogen, —CH$_3$, —CH$_2$OCH$_3$, —C(O)NH$_2$, —CH$_2$C(O)NH$_2$, —OCH$_3$, —NH$_2$ or —NHCH$_2$CH$_3$; and
X–X' and Y–Y' are —CH$_2$—CH$_2$—.

32. The compound of formula I according to claim 18 selected from
1-[7-(3-fluoro-benzyloxy)-1,2,4,5-tetrahydro-benzo[d]azepin-3-yl]-ethanone,
1-[7-(3-fluoro-benzyloxy)-1,2,4,5-tetrahydro-benzo[d]azepin-3-yl]-2-methoxy-ethanone,
2-[7-(3-fluoro-benzyloxy)-1,2,4,5-tetrahydro-benzo[d]azepin-3-yl]-2-oxo-acetamide,
3-[7-(3-fluoro-benzyloxy)-1,2,4,5-tetrahydro-benzo[d]azepin-3-yl]-3-oxo-propionamide,
7-(3-fluoro-benzyloxy)-1,2,4,5-tetrahydro-benzo[d]azepine-3-carboxylic acid methyl ester,
7-(3-fluoro-benzyloxy)-1,2,4,5-tetrahydro-benzo[d]azepine-3-carbaldehyde,
7-(3-fluoro-benzyloxy)-3-methanesulfonyl-2,3,4,5-tetrahydro-1H-benzo[d]azepine,
7-(3-fluoro-benzyloxy)-1,2,4,5-tetrahydro-benzo[d]azepine-3-carboxylic acid amide,
7-(3-fluoro-benzyloxy)-1,2,4,5-tetrahydro-benzo[d]azepine-3-carboxylic acid ethylamide;
2-[7-(3-fluoro-benzyloxy)-1,2,4,5-tetrahydro-benzo[d]azepin-3-yl]-acetamide, and
(RS)-2-[7-(3-fluoro-benzyloxy)-1,2,4,5-tetrahydro-benzo[d]azepin-3-yl]-propionamide.

33. A process for the preparation of a compound of formula I in accordance with claim 18

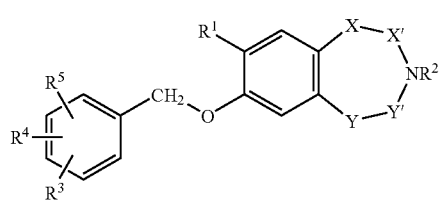

wherein
R$^1$ is hydrogen or methyl;
R$^2$ is —CH$_2$C(O)NH$_2$, —CH(CH$_3$)C(O)NH$_2$, —S(O)$_2$CH$_3$ or —C(O)R$^6$;
R$^3$, R$^4$ and R$^5$ are each independently hydrogen, halogen, cyano, (C$_1$–C$_3$)-alkyl or —O—(C$_1$–C$_3$)-alkyl;
R$^6$ is hydrogen, —CH$_3$, —CH$_2$OCH$_3$, —C(O)NH$_2$, —CH$_2$C(O)NH$_2$, —OCH$_3$, —NH$_2$ or —NHCH$_2$CH$_3$;
X–X' is —CH$_2$—CH$_2$— or —CH=CH—; and
Y–Y' is —CH$_2$—CH$_2$— or —CH=CH—; or wherein when one of X–X' and Y–Y' is —CH$_2$—CH$_2$— and the other is —CH=CH—, or when both of X–X' and Y–Y' are —CH=CH—, then R$^2$ is —S(O)$_2$CH$_3$ or —C(O)R$^6$;
comprising reacting a compound of formula III

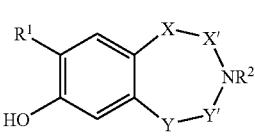

with a compound of formula IV

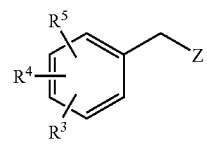

wherein Z is OH, or, when R$^2$ is —S(O)$_2$CH$_3$ or —C(O)R$^6$, then Z may also be halogen or a sulfonic acid residue.

34. A process for the preparation of a compound of formula I in accordance with claim 18

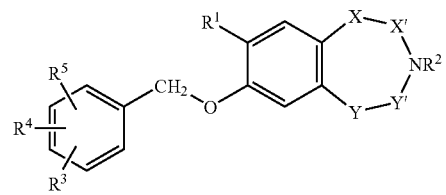

wherein
R$^1$ is hydrogen or methyl;
R$^2$ is —S(O)$_2$CH$_3$ or —C(O)R$^6$;
R$^3$, R$^4$ and R$^5$ independently are hydrogen, halogen, cyano, (C$_1$–C$_3$)-alkyl or —O—(C$_1$–C$_3$)-alkyl;
R$^6$ is hydrogen, —CH$_3$, —CH$_2$OCH$_3$, —OCH$_3$, —NH$_2$ or —NHCH$_2$CH$_3$;
X–X' is —CH$_2$—CH$_2$— or —CH=CH—; and
Y–Y' is —CH$_2$—CH$_2$— or —CH=CH—;
comprising reacting a compound of formula I wherein R$^2$ is hydrogen, with an activated acyl derivative; or by a condensation reaction of an acid using a condensation reagent; or by reaction with an activated sulfonyl derivative; or by reaction with an isocyanate.

35. A process for the preparation of a compound of formula I in accordance with claim 18

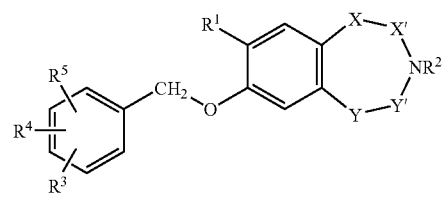

wherein
R$^1$ is hydrogen or methyl;

R² is —S(O)₂CH₃ or —C(O)R⁶;
R³, R⁴ and R⁵ independently are hydrogen, halogen, cyano, (C₁–C₃)-alkyl or —O—(C₁–C₃)-alkyl;
R⁶ is —C(O)NH₂ or —CH₂C(O)NH₂,
X–X' is —CH₂—CH₂— or —CH═CH—; and
Y–Y' is —CH₂—CH₂— or —CH═CH—; or
comprising reacting a compound of formula I wherein R² is hydrogen, with an activated acyl derivative; or by a condensation reaction of an acid using a condensation reagent; and converting the resulting ester function into a corresponding amide.

36. A process for the preparation of a compound of formula I in accordance with claim 18

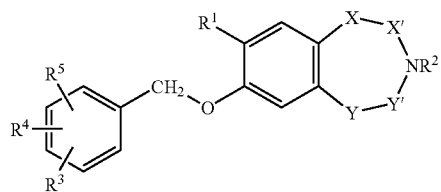

R¹ is hydrogen or methyl;
R² is (C₁–C₃)-alkyl, —CH₂C(O)NH₂ or —CH(CH₃)C(O)NH₂;
R³, R⁴ and R⁵ independently are hydrogen, halogen, cyano, (C₁–C₃)-alkyl or —O—(C₁–C₃)-alkyl;
X–X' is —CH₂—CH₂— or —CH═CH— and
Y–Y' is —CH₂—CH₂— or —CH═CH—; or
wherein X–X' and Y–Y' are not —CH═CH— at the same time, or X–X' and Y–Y' are not —CH₂—CH₂— when the other is —CH═CH—;
comprising reacting a compound of formula I wherein R² is hydrogen, with an alkylating agent selected from the group consisting of alkylating agents include halides, tosylates, mesylates and triflates.

37. A pharmaceutical composition comprising a compound of formula I

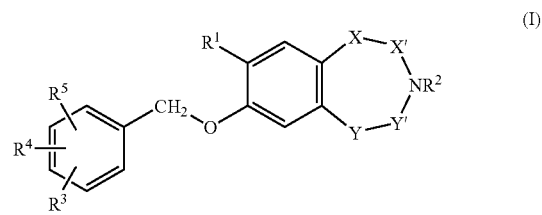 (I)

wherein
R¹ is hydrogen or methyl;
R² is —CH₂C(O)NH₂, —CH(CH₃)C(O)NH₂, —S(O)₂CH₃ or —C(O)R⁶;
R³, R⁴ and R⁵ are each independently hydrogen, halogen, cyano, (C₁–C₃)—alkyl or —O—(C₁–C₃)—alkyl;
R⁶ is hydrogen, —CH₃, —CH₂OCH₃, —C(O)NH₂, —CH₂C(O)NH₂, —OCH₃, —NH₂ or —NHCH₂CH₃,
X–X' is —CH₂—CH₂— or —CH═CH—; and
Y–Y' is —CH₂—CH₂— or —CH═CH—;
wherein when one of X–X' and Y–Y' is —CH₂—CH₂— and the other is —CH═CH—, or when both of X–X' and Y–Y' are —CH═CH—, then R² is —S(O)₂CH₃ or —C(O)R⁶;
or a pharmaceutically acceptable salt thereof
and a pharmaceutically acceptable diluent or carrier therefor.

* * * * *